United States Patent
Anash

(10) Patent No.: US 11,918,825 B2
(45) Date of Patent: Mar. 5, 2024

(54) COMPOSITIONS, DEVICES, SYSTEMS, KITS AND METHODS FOR THE TREATMENT OF A SKIN CONDITION

(71) Applicant: CLEARSKIN LTD., Karmiel (IL)

(72) Inventor: Milana Anash, Karmiel (IL)

(73) Assignee: ClearSkin Ltd., Karmiel (IL)

( * ) Notice: Subject to any disclaimer, the term of this patent is extended or adjusted under 35 U.S.C. 154(b) by 157 days.

(21) Appl. No.: 16/975,276

(22) PCT Filed: Feb. 13, 2019

(86) PCT No.: PCT/IL2019/050169
§ 371 (c)(1),
(2) Date: Aug. 24, 2020

(87) PCT Pub. No.: WO2019/162935
PCT Pub. Date: Aug. 29, 2019

(65) Prior Publication Data
US 2021/0370089 A1    Dec. 2, 2021

Related U.S. Application Data

(60) Provisional application No. 62/634,812, filed on Feb. 24, 2018, provisional application No. 62/634,811, filed on Feb. 24, 2018.

(51) Int. Cl.
| | | |
|---|---|---|
| *A61K 35/741* | (2015.01) | |
| *A61K 9/00* | (2006.01) | |
| *A61K 35/74* | (2015.01) | |
| *A61K 47/46* | (2006.01) | |
| *A61N 5/06* | (2006.01) | |

(52) U.S. Cl.
CPC .......... *A61N 5/0616* (2013.01); *A61K 9/0014* (2013.01); *A61K 35/74* (2013.01); *A61K 47/46* (2013.01); *A61N 5/0624* (2013.01); *A61N 2005/0645* (2013.01); *A61N 2005/0652* (2013.01); *A61N 2005/0659* (2013.01); *A61N 2005/0661* (2013.01); *A61N 2005/0663* (2013.01)

(58) Field of Classification Search
CPC ................................. A61K 35/741
See application file for complete search history.

(56) References Cited

U.S. PATENT DOCUMENTS

| | | | | |
|---|---|---|---|---|
| 4,943,432 A | * | 7/1990 | Biener | A61K 33/00 424/647 |
| 2014/0044677 A1 | | 2/2014 | Qvit-Raz et al. | |
| 2014/0094879 A1 | * | 4/2014 | Van Os | A61N 5/0613 607/88 |
| 2015/0079040 A1 | | 3/2015 | O'Neill et al. | |
| 2016/0008412 A1 | * | 1/2016 | Putaala | A61K 35/744 424/93.4 |
| 2016/0101294 A1 | | 4/2016 | Sun et al. | |
| 2017/0119827 A1 | | 5/2017 | Kovarik | |
| 2017/0281660 A1 | * | 10/2017 | Zapka | A61P 31/02 |

FOREIGN PATENT DOCUMENTS

| | | | | |
|---|---|---|---|---|
| FR | 2996452 A1 | * | 4/2014 | ............... A61K 8/99 |
| WO | 2005030230 A1 | | 4/2005 | |
| WO | 2006013441 A2 | | 2/2006 | |
| WO | 2012150269 A1 | | 11/2012 | |
| WO | 2016124266 A1 | | 8/2016 | |

OTHER PUBLICATIONS

Ataiekhorasgani et al., "Streptomyces infection in Cushing syndrome: A case report and literature review," Advanced Biomedical Research 3 26:1-4, 2014.*
Ouwehand et al., "Probiotics for the skin: a new area of potential application?" Letters in Applied Microbiology 36:327-331, 2003.*
Int'l Search Report for PCT/IL2019/050169, dated Apr. 18, 2019.
Kukkonen et al. (2007). Probiotics and prebiotic galacto-oligosaccharides in the prevention of allergic diseases: a randomized, double-blind, placebo-controlled trial. Journal of Allergy and Clinical Immunology, 119 (1), Jan. 1, 2007, doi: 10.1016/j.jaci.2006.09.009. Epub Oct. 23, 2006. PMID: 17208601.
Di Marzo et al. (2003). Effect of the lactic acid bacterium *Streptococcus thermophilus* on stratum corneum ceramide levels and signs and symptoms of atopic dermatitis patients. Experimental Dermatology. Oct. 2003; 12(5):615-20. doi: 10.1034/j.1600-0625.2003.00051.x. PMID: 14705802.
Blanchet-Réthoré et al. (2017). Effect of a lotion containing the heat-treated probiotic strain Lactobacillus johnsonii NCC 533 on *Staphylococcus aureus* colonization in atopic dermatitis. Clinical, Cosmetic and Investigational Dermatology Jul. 3, 2017;10:249-257. doi: 10.2147/CCID.S135529. PMID: 28721083; PMCID: PMC5501445.
Torsekar et al. (2017). Topical therapies in psoriasis. Indian Dermatology Online Journal Jul.-Aug. 2017;8(4):235-245. doi: 10.4103/2229-5178.209622. PMID: 28761838; PMCID: PMC5518573.
Supplementary Search Report and Opinion for EP3755356 Completed Oct. 18, 2021, dated Feb. 1, 2022 20 pages.
Partial Search Report for EP3755356 dated Oct. 29, 2021 13 pages.

* cited by examiner

*Primary Examiner* — Rosanne Kosson
(74) *Attorney, Agent, or Firm* — The Roy Gross Law Firm, LLC; Roy Gross

(57) ABSTRACT

A multi-component regimen for the treatment of a skin condition including administering at least two components of at least one galenic microbial composition, applying at least one acidic composition, applying at least one mineral salt composition, illuminating an area of the skin and heating an area of the skin. The regimen includes at least one of administering at least one galenic microbial composition and illuminating an area of the skin. Also provided is a galenic microbial composition including bacteria of the phylum *Actinobacterium* and a dermatologically compatible carrier. Further provided is a wearable cutaneous-treatment device for the therapeutic illumination of mammalian skin when activated, to project light outwards from h inner surface to illuminate at least a portion the area of skin.

4 Claims, 9 Drawing Sheets

COMPOSITIONS, DEVICES, SYSTEMS, KITS AND METHODS FOR THE TREATMENT OF A SKIN CONDITION

FIELD OF THE INVENTION

The invention, in some embodiments, relates to the field of treatment of skin conditions, and more particularly to compositions, devices, systems, kits and methods for the treatment of skin conditions such as psoriasis.

BACKGROUND

The skin, which is the largest organ of the body, serves to cover and protect the body. Factors such as allergies, irritants, genetic factors and skin conditions can result in irritation, clogging or inflammation of the skin, causing symptoms such as rashes, redness, swelling, burning or itching.

Common skin conditions include psoriasis, acne, dermatitis, rosacca and eczema.

Psoriasis is a skin disease affecting around 125 million people worldwide and causing medical, financial and human burden to psoriasis patients. The physical and psychological effects of psoriasis can be debilitating, with patients suffering from scaly red plaques and peeling on visible parts of the body. Psoriasis is caused by overly rapid division of skin cells, accompanied by painful inflammation.

Psoriasis vulgaris is an incurable chronic skin disease, characterized by recurring plaques. Even if the symptoms of the disease are reduced or cleared during treatment, they frequently reappear on another area of the skin.

The currently available options for treatment of psoriasis include phototherapy, administration of topical preparations containing corticosteroids, vitamin D analogues or retinoids; systemic drug administration; and Dead Sea climatotherapy. These treatment options have various degrees of efficacy and some undesired side effects. Furthermore, Dead Sea climatotherapy requires the subject to be physically present in the region of the Dead Sea, thus involving loss of working days, travel expenses, board and lodging expenses.

Background art includes US Publication Nos. US 2005/0196480, US 2006/0171936, US 2009/0258085, US 2011/0014248, US 2011/0189133, US 2012/0101557, US 2014/0005266, US 2014/0074010, US 2016/0148558, US 2014/021513, US 2015/0079040, US 2015/0290479, US 2016/0129279, US 2016/0256706, US 2016/0317432 and US 2016/0367834; US Patent Nos. U.S. Pat. Nos. 4,943,432, 4,996,046, 5,358,503, 6,290,713, 6,596,016, 7,304,201, 7,498,049, 7,921,853, 8,339,058, 8,481,299, 9,339,667. U.S. Pat. Nos. 9,370,449 and 9,533,170; PCT Publication Nos. WO 2001/000218, WO 2003/047682, WO 2005/030230, WO 2006/013441, WO 2012/150269, WO 2016/166599, WO 2016/176380, WO 2017/019455 and WO 2017/030436; and European Publication No. EP 2044973 A1.

Non-patent background art includes:
https://www.nchi.nlm.nih.gov/pmc/articles/PMC4946393/S (2016)
https://solarcsystems.con/en/?v=88588bacf0da
http://redlighttherapy.lighttherapyoptions.com/red-light-therapy-reviews/
http://www.eurocept-honecare.nl/files/Image/Licht/Philips-BlueControl_user-manual.pdf
https://www.researchgate.net/publication/224037385 Scientific Evidence of the Therapeutic Effects of Dead Sea Treatments A Systematic Review
Int J Dermatol. 2005 February; 44(2):151-7 (2015)
https://wellnessmama.com/9166/sea-salt-spray/
ARPN Journal of Engineering and Applied Science, vol. 10(21), pages 9913-9918
Biomedical Optics Express, vol. 4(12), pages 2925-2937 (2013)

SUMMARY OF THE INVENTION

Some embodiments of the invention relate to compositions, devices, systems, kits and methods for the treatment of skin conditions such as psoriasis.

Aspects and embodiments of the invention are described in the specification herein below and in the appended claims.

According to an aspect of some embodiments of the present invention, there is provided a multi-component regimen for the treatment of a skin condition in a subject in need thereof, the regimen comprising, in no particular order, at least two components selected from the group consisting of:
administering at least one galenic microbial composition to the subject;
applying at least one acidic composition to an area of skin of the subject;
applying at least one mineral salt composition to an area of skin of the subject;
illuminating an area of skin of the subject; and
heating of an area of skin of the subject,
wherein the regimen comprises at least one of administering at least one galenic microbial composition to the subject or illuminating an area of skin of the subject, thereby treating the skin condition.

According to some embodiments, the skin condition is a cosmetic condition, i.e. the treatment relates solely to aesthetic aspects of a skin condition. According to some such embodiments, the treatment is a non-medical treatment.

According to an aspect of some embodiments of the present invention, there is provided a galenic microbial composition for use in the treatment of a skin condition, the composition configured for use together with at least one additional component selected from the group consisting of applying at least one acidic composition to an area of skin of the subject; applying at least one mineral salt composition to an area of skin of the subject; illuminating an area of skin of the subject; and heating of an area of skin of the subject.

According to some embodiments, the galenic microbial composition is a pharmaceutical microbial composition.

According to some embodiments, the galenic microbial composition is a cosmetic microbial composition.

According to some embodiments, the galenic microbial composition is a composition comprising a microorganism selected from the group consisting of bacteria, fungi, algae, viruses and yeast, or a product derived from such a microorganism. According to some preferred embodiments, the galenic microbial composition is a bacterial composition.

According to an aspect of some embodiments of the present invention, there is provided the use of a galenic microbial composition for the manufacture of a medicament for use in a multi-component regimen for the treatment of a skin condition, the medicament configured for use together with at least one additional component selected from the group consisting of applying at least one acidic composition to an area of skin of the subject; applying at least one mineral salt composition to an area of skin of the subject; illuminating an area of skin of the subject; and heating of an area of skin of the subject.

According to some embodiments, at least two of: administering of the at least one galenic microbial composition, applying at least one acidic composition to an area of skin of the subject, applying at least one mineral salt composition to an area of skin of the subject, illuminating an area of skin of the subject and heating of an area of skin of the subject are carried out independently, sequentially, simultaneously or concomitantly, or any combination thereof. For example, two or more steps of the multi-component regimen may be carried out substantially simultaneously, while additional steps are carried out sequentially.

According to some embodiments, administering of the at least one galenic microbial composition, applying of the at least one acidic composition and applying of the at least one mineral composition are carried out independently, sequentially, simultaneously or concomitantly, or in a single composition, or any combination thereof.

According to an exemplary embodiment, the multi-component regimen may comprise first applying at least one mineral composition, followed by illuminating an area of skin, followed by applying at least one galenic microbial composition.

According to some embodiments, the multi-component regimen comprises administering a galenic microbial composition, and applying at least one composition selected from the group consisting of an acidic composition and a mineral composition to the skin of the subject. In some such embodiments, the multi-component regimen further comprises illuminating and/or heating an area of skin of the subject.

According to some embodiments, the multi-component regimen comprises administering at least one composition selected from the group consisting of a galenic microbial composition, an acidic composition and a mineral composition to the subject and illuminating and/or heating an area of skin of the subject.

According to some embodiments, the multi-component regimen comprises administering a galenic microbial composition and at least one composition selected from the group consisting of an acidic composition and a mineral composition to the subject; and illuminating and/or heating an area of skin of the subject.

According to some embodiments, the multi-component regimen comprises administering a galenic microbial composition and an acidic composition to the subject. In some such embodiments, the multi-component regimen further comprises illuminating and/or heating an area of skin of the subject.

According to some embodiments, the multi-component regimen comprises administering a galenic microbial composition and a mineral composition to the subject. In some such embodiments, the multi-component regimen further comprises illuminating and/or heating an area of skin of the subject.

According to some embodiments, the multi-component regimen comprises administering a galenic microbial composition, an acidic composition and a mineral composition to the subject. In some such embodiments, the multi-component regimen further comprises illuminating and/or heating an area of skin of the subject.

According to some embodiments, the multi-component regimen comprises illuminating and heating an area of skin of the subject.

According to some embodiments, the multi-component regimen comprises administering a galenic microbial composition and illuminating an area of skin of the subject.

According to some embodiments, the multi-component regimen comprises applying an acidic composition and illuminating an area of skin of the subject.

According to some embodiments, the multi-component regimen comprises applying a mineral composition and illuminating an area of skin of the subject.

According to some embodiments, the multi-component regimen comprises applying an acidic composition and a mineral composition; and illuminating an area of skin of the subject.

According to some embodiments, the multi-component regimen comprises administering a galenic microbial composition, applying an acidic composition, applying a mineral composition and illuminating an area of skin of the subject.

According to some embodiments, the frequency at which the multi-component regimen is applied to a subject is four times per day, three times per day, twice a day, once a day, six times per week, five times per week, four times per week, three times per week, twice per week, once weekly, three times per month, twice per month, or once monthly.

According to some embodiments, the at least two components of the multi-component regimen are each applied substantially simultaneously, or subsequently, wherein the second component is applied substantially immediately after the first component.

According to some embodiments wherein three or more components of the multi-component regimen are applied, all components may be applied substantially simultaneously or subsequently, wherein each component is applied substantially immediately after the preceding component.

According to some embodiments wherein three or more components of the multi-component regimen are applied, two components may be applied substantially simultaneously and a third component applied substantially immediately after the preceding components.

According to some embodiments, two or more components of the multi-component regimen may be applied at any suitable interval. For example, a second component may be applied 5 minutes, 10 minutes, 20 minutes, 30 minutes, 40 minutes, one hour, two hours, three hours, four hours, six hours, eight hours, 12 hours or 24 hours after a first component.

According to some embodiments, two or more components of the multi-component regimen may each be applied on alternating days, wherein a first component is applied on days 1, 3, 5 etc., and a second component is applied on days 2, 4, 6, etc.

According to some embodiments, the galenic bacterial composition comprises a biological ingredient selected from the group consisting of bacteria, a substance produced by bacteria, and any combination thereof.

According to some embodiments, the microorganisms of the microbial composition are selected from the group consisting of *Proteobacteria, Propionibacterium, Corynebacterium, Actinomycetales, Clostridiales, Lactobacillales, Staphylococcus, Bacteroidales, Flavobacteriales, Actinobacteria, Firmicutes, Stafilacocci, Brevibacterium, Propionibacteria acnes, Micrococcus luteus, Aspergillus, Bacillus, Bacteroides,*

According to some embodiments, microorganisms are selected from the group consisting of *Aspergillus niger, Aspergillus oryza, Bacillus coagulans, Bacillus lentus, Bacillus licheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium infantis, Bifidobacterium longum, Bifido-*

*bacterium thermophilum, Lactobacillus acidolphilus, Lactobacillus brevis, Lactobacillus buchneri, Lactobacillus bulgaricus, Lactobacillus casei, Lactobacillus curvatus, Lactobacillus delbrueckii, Lactobacillus fermentum, Lactobacillus helveticus, Lactobacillus lactis, Lactobacillus plantarum, Lactobacillus euterii, Leuconostoc mesenteroides, Pediococcus acidilacticii, Pediococcus cervisiae, Pediococcus pentosaceus, Propionibacterium freudenreichii, Propionibacterium shermanii, Saccharomyces cerevisiae, Entercococcus cremoris, Entercococcus diacetylactis, Entercococcus faecium, Entercococcus intermedius, Entercococcus lactis, Entercococcus thermophilius* and *Lactobacillus cellobiosus*.

According to some embodiments, the bacteria comprise bacteria of the phylum *Actinobacterium*.

According to an aspect of some embodiments of the present invention, there is provided a galenic microbial composition comprising bacteria of the phylum *Actinobacterium*.

According to some embodiments, the galenic microbial composition of the present invention is suitable for use as a component in the multi-component regimen disclosed herein.

According to an aspect of some embodiments of the present invention, there is provided a galenic microbial composition comprising bacteria of the phylum *Actinobacterium* for use in the treatment of a skin condition.

According to an aspect of some embodiments of the present invention, there is provided the use of a galenic microbial composition comprising bacteria of the phylum *Actinobacterium* for the manufacture of a medicament for treating a skin condition.

According to some embodiments of the multi-component regimen or the galenic microbial composition, the bacteria of the phylum *Actinobacterium* comprises bacteria of a genus selected from the group consisting of *Propionibacterium, Brevibacterium, Micrococcus* and any combination thereof.

According to some embodiments of the multi-component regimen or the galenic microbial composition, the *Propionibacteria* comprise bacteria of a species selected from the group consisting of *Propionibacterium freudenreichii, Propionibacterium* acne and combinations thereof.

According to some embodiments of the multi-component regimen or the galenic microbial composition, the *Proponibacterium freudenreichii* comprise bacteria of the subspecies *Propionibacterium shermanii*.

According to some embodiments of the multi-component regimen or the galenic microbial composition, the *Propionibacterium shermanii* are of the strain ATCC 9614/DSM 4902/CIP 103027/NCIMB 8099/CIRM-BIA1; NCTC 13653.

According to some embodiments of the multi-component regimen or the galenic microbial composition, *Micrococcus* bacteria comprise bacteria of the species *Micrococcus luteus*.

According to some embodiments of the multi-component regimen or the galenic microbial composition, the bacteria disclosed herein are living bacteria.

According to some embodiments of the multi-component regimen or the galenic microbial composition, the bacteria disclosed herein are non-living bacteria.

According to some embodiments, the galenic microbial composition comprises a product of bacteria, such as a fermentation product or a degradation product.

According to some embodiments, the galenic microbial composition disclosed herein comprises a carrier. In some such embodiments, the carrier comprises an oily ingredient. In other such embodiments, the carrier is, or comprises a non-oily carrier Non-limiting examples of oily ingredients include, for example, hydrocarbons, esters, animal and vegetable oils and fats, waxes, goby oils, higher fatty acids, higher alcohols, silicone type substances, sterols, and resins as well as those obtained by enzymatically (for instance, hydrolysis and transesterification) or chemically (for instance, transesterification and hydrogenation) treating the foregoing substances.

Specific examples thereof include almond oil, apricot kernel oil, argan oil, avocado oil, baobab oil, camelina oil, carrot oil, castor oil, citronella oil, coconut oil, cranberry seed oil, grape seed oil, hemp seed oil, jojoba oil, macadamia nut oil, meadowfoam seed oil, oat emollient, red raspberry seed oil, rosehip oil, soybean oil, rape seed oil, corn oil, sesame seed oil, cotton seed oil, safflower oil, sunflower oil, peanut oil, rice germ oil, wheat germ oil, husked rice germ oil, Job's tears (*Coix lachryma-jobi* Linn.) oil, macademia nut oil, garlic oil, camellia oil, palm oil, olive oil, jojoba oil, macademia nut oil, avocado oil, castor oil, linseed oil, beefsteak plant oil, eucalyptus oil, evening primrose oil, turtle oil, mink oil, lard, beef tallow, equine oil, snake oil, fish oil, egg oil, egg yolk oil, liquid paraffin, isoparaffin, vaseline, squalane, squalene, turpentine oil, polyethylene glycol, isopropyl myristatc, isopalmityl myristate, 2-octyldodecyl myristate, cetyl 2-ethylhexanoate, glyceryl tri-2-ethylhexanoate, glyceryl tricaprylate, triglycerides of mixed fatty acids of caprylic and capric acids, neopentyl glycol di-2-ethylhexanoate, diisostearyl malate, isononyl isononanoate (3,5,5-trimethylhexyl-3',5',5'-trimethylhexanoate), cholesteryl 12-hydroxystearate, monoesters to hexaesters of dipentaerythritol and isostearic acid and/or higher fatty acids, glyceryl esters of p-mcthoxycinnamic acid and 2-ethylhexanoic acid, isooctyl p-methoxycinnamate, glyceryl tristearate, rosin, cholesterol, phytosterols (such as campesterol, stigmasterol and sitosterol), orange raffinate, lanolin, myristic acid, palmitic acid, isopalmitic acid, stearic acid, isostearic acid, oleic acid, linolic acid, linoleic acid, ricinoleic acid, 12-hydroxystearic acid, 10-hydroxystearic acid, behenic acid, crucic acid, arachidonic acid, cicosapentaenoic acid, docosahexaenoic acid, myristyl alcohol, cetyl alcohol, stearyl alcohol, isostearyl alcohol, behenyl alcohol, lanolin alcohol, paraffin waxes, microcrystalline waxes, ceresine waxes, becs wax, shea butter, vaseline, hard fats, carnauba wax, candelilla wax, rice wax, rice bran wax, sunflower wax, berry wax, myrica fruit wax, laurel wax, Japan wax (also known as sumac wax), shellac, dimethylpolysiloxane, methylphenyl-polysiloxane and essential oils derived from animals and vegetables, or any combination thereof.

According to some embodiments, the oily ingredient is selected from the group consisting of one or more plant oils, one or more vegetable oils, one or more essential oils, one or more butters, one or more waxes and combinations thereof.

According to some embodiments, the carrier is a water-soluble ointment base.

According to some embodiments, the carrier comprises at least one polyethylene glycol.

According to some embodiments, the oily ingredient is selected from the group consisting of olive oil, a plant-derived butter (such as shea butter), a natural wax (such as bees wax), pomegranate oil, rosehip oil and any combinations thereof.

According to some preferred embodiments, the oily ingredient comprises a combination of olive oil, shea butter and beeswax.

According to some preferred embodiments, the oily ingredient comprises a combination of olive oil, pomegranate oil, rosehip oil, geranium oil and rose flower oil.

According to some embodiments, the galenic microbial composition further comprises an excipient, such as, for example, a thickener, a gelling agent, a neutralizer, an occlusive, an antioxidant, a buffering agent, a pH adjusting agent, a filler, an emulsifying agent (also referred to herein as an emulsifier), a co-emulsifier, an emollient, a solvent, a stabilizing agent (also referred to herein as a stabilizer), a solublilizer, a stiffening agent, a suspending agent, a binder, a viscosity-increasing agent, a penetration enhancer, a preservative, a chelating agent, a disintegrant, a plasticizer, a humectant, a fragrance and the like.

According to some embodiments, the galenic microbial composition disclosed herein comprises an antioxidant. In some embodiments, the antioxidant is a hydrophilic antioxidant. In some embodiments, the antioxidant is a lipophilic antioxidant.

Non-limiting examples of hydrophilic antioxidants include, for example, ascorbic acid (vitamin C), glutathione, lipoic acid and uric acid.

Non-limiting examples of lipophilic antioxidants include, for example, tocopherol (vitamin E), butylated hydroxytoluene (BHT), butylated hydroxyanisole (BHA), carotenes and ubiquinol (coenzyme Q). In some embodiments, the antioxidant protects the galenic carrier, active principle or the entire composition from the effects of oxidation. Non-limiting examples of gelling agents include tragacanth, sodium alginate, pectin, silicates (such as fumed silica), gelatin, cellulose derivatives (such as methyl cellulose, hydroxypropyl methyl cellulose, carboxyl methyl cellulose), a carbomer, guar gum, polyvinyl alcohol clay and the like.

Non-limiting examples of penetration enhancers include oleic acid, lecithin, urea, clove oil, isopropyl myristate, menthol, carvacrol, linalool, limonene, geraniol, nerolidol, propylene glycol diperlargonate and cyclodextrins.

Non-limiting examples of antimicrobial preservatives include methyl hydroxybenzoate, propyl hydroxybenzoate, chlorocresol, benzoic acid, phenyl mercuric nitrate, benzalkonium chloride, chlorhexidine actetate, benzyl alcohol and mercurial.

Non-limiting examples of chelating agents include citric acid and maleic acid.

Non-limiting examples of humectants include polyethylene glycol, glycerol and sorbitol.

Non-limiting examples of fragrances include lavender oil, rose oil, lemon oil, lime oil, bergamot oil, orange oil, petitgrain oil, tangerine oil, chamomile oil, cinnamon oil, clary sage oil, cypress oil, geranium oil, ginger oil, juniper oil, marjoram oil, myrtle oil, neroli oil, pine oil, rosewood oil, ylang ylang oil, cedarwood oil, jasmine oil, frankincense oil, myrrh oil, patchouli oil, sandalwood oil and spikenard oil.

Non-limiting examples of emulsifiers include anionic emulsifiers (such as alkyl sulfates, soaps, dodecyl benzene sulfonate, lactylates, sulfosuccinates, monoglyceride sulfonates, phosphate ester, silicones and taurates); cationic emulsifiers (such as quaternary ammonium compounds and alkoxyalkamines); and non-ionic emulsifiers (such as poyloxyethylene alkyl-aryl ethers, polyoxyethylene fatty acid esters, sorbitan fatty acids esters, glyceryl fatty acid esters, sucrose fatty acid esters and polyoxyethylene-polyoxypropylene block polymers).

According to some embodiments, the galenic microbial composition disclosed herein comprises *Propionibacterium shermanii* and an oily ingredient.

According to some embodiments, the galenic microbial composition disclosed herein comprises *Propionibacterium shermanii* and a water-soluble ointment base, or a non-oily carrier (also referred to herein as a diluent) comprising water or aloe vera leaf juice or a combination thereof. In some such embodiments, the galenic bacterial composition further comprises at least one excipient selected from the group consisting of a thickener (such as sclerotium gum), a preservative (such as salicylic acid or citric acid, or a combination thereof), a neutralizer (such as sodium gluconate), a humectant (such as saccharide isomerate, cetearyl wheat straw, or a combination thereof), an emulsifier (such as a glucoside, cetearyl, or a combination thereof), an occlusive (such as coconut oil, olea Europea fruit oil, or a combination thereof), a co-emulsifier (such as cetyl alcohol), an antioxidant (such as tocopherol), and a fragrance (such as *Lavendula Angustifolia*, Rosa damascene extract, or a combination thereof).

According to some embodiments, the bacteria are present in the galenic microbial composition in a concentration of from about 0.0002% (w/w) to about 20% (w/w) of the total composition. In some preferred embodiments, the bacteria are present at a concentration of from about 6% to about 7% (w/w) of the total composition. In some embodiments, the bacteria are provided as a freeze-dried powder.

According to an aspect of some embodiments of the present invention, there is provided a galenic microbial composition comprising *Propionibacterium shermanii*, olive oil, geranium oil, rose flower oil, and tocopherol. In some such embodiments, the galenic microbial composition comprises from about 6 to about 7% (w/w) bacteria. In some such embodiments, the galenic microbial composition comprises from about 90 to about 95% (w/w) olive oil, from about 0.005 to about 0.05% (w/w) geranium oil, from about 0.001 to about 0.1% (w/w) rose flower oil and from about 0.01 to about 1% (w/w) tocopherol. In some such embodiments, the galenic microbial composition is for use in a method for the treatment of a skin condition. In some embodiments, there is provided the galenic microbial composition for use in the treatment of a skin condition. According to an exemplary embodiment, the galenic microbial composition consists essentially of 6.685% (w/w) bacteria; 92.8% (w/w) olive oil; 0.5% (w/w) tocopherol; 0.01% (w/w) geranium oil; and 0.005% (w/w) rose flower oil.

According to some embodiments, the galenic microbial composition disclosed herein comprises a mixture of *Brevibacterium, Propionibacterium acnes* and *Micrococcus luteus*; and an oily ingredient.

According to some embodiments, the galenic microbial composition disclosed herein is a topical composition i.e. a composition suitable for topical administration. The composition for topical administration may be provided in the form of a solution, a suspension, an emulsion, a lotion, a cream, a liniment, a balm, an ointment, a gel, a foam, a patch, a plaster, a powder, a paste (including a fatty paste or a non-greasy paste), a paint, a poultice, a tincture, an emulgel (comprising an emulsion in a gel base), or the like, or any combination thereof.

Non-limiting examples of excipients for a semi-solid dosage form include a base, an antimicrobial preservative, a humectant, an antioxidant, an emulsifier, a gelling agent, a penetration enhancer, a buffer and a fragrance.

Non-limiting examples of excipients for a gel formulation include carbomer (as a thickener), disodium EDTA (as a pH adjustment agent), glycerin (as a humectant), benzophenone-4 (as a stabilizer), diazolidinyl urea and/or iodopropynyl butylcarbamate (as a preservative), PVP K-90 and/or PVP/dimethylaminoethylmethacrylate copolymer, oleth-20 (as a solubilizer), a fragrance, aminomethylpropanol (as a neutralizer) and water as solvent. Non-limiting examples of excipients for a cream include medium chain triglycerides (as an emollient/emulsifying agent/solvent), olelyl alcohol (as an emollient/emulsifying agent/penetration enhancer), propylene glycol (as a humectant/solvent), cetyl alcohol (as an emulsifier), stearyl alcohol (as a stiffening agent), glyceryl monostearate (as an emollient/emulsifier), sodium cotostearyl (as an emulsifier), benzyl alcohol (as a preservative), citric acid and/or sodium hydroxide (as a pH adjusting agent) and water as solvent.

Non-limiting examples of excipients for an ointment include sodium lauryl sulfate, propylene glycol, stearyl alcohol, white petrolatum, methyl hydroxybenzoate, propyl hydroxybenzoate, salicylic acid and water.

A base for an ointment may be an oleaginous base (comprising oleaginous materials such as water-insoluble hydrophobic oils and fats), an absorption base (water in oil emulsion, such as comprising a mixture of animal sterols with petrolatum), an emulsion base, a water-soluble base (generally comprising polyethylene glycols or one or more hydrocolloids) or a water removable base.

A non-limiting example of a base for a hydrophilic ointment (oil in water type emulsion base) comprises white petrolatum, stearyl alcohol, propylene glycol, sodium lauryl sulphate and water.

A non-limiting example of a base for a cold cream (water in oil emulsion base) comprises white wax, cetyl esters wax, mineral oil, sodium borate and water.

A non-limiting example of a paste base comprises zinc oxide, starch, white petrolatum and salicylic acid.

The composition may be provided in a delivery form comprising a plaster, i.e. a solid or semi-solid mass which adheres to the skin, comprising, for example, cotton or muslin as a backing material.

According to alternative embodiments, the galenic microbial composition is provided in a dosage form suitable for oral administration, such as, for example, as a pill, tablet, capsule, syrup, solution, suspension, powder or the like, or any combination thereof.

According to alternative embodiments, the galenic microbial composition is provided in a form suitable for administration by inhalation, such as, for example, in an aerosol, inhaler, nebulizer, vaporizer or the like, or any combination thereof.

According to some alternative embodiments, the galenic microbial composition is provided in a form suitable for parenteral administration, such as for example, for administration by intradermal, subcutaneous, intramuscular, intraosseous, intraperitoneal or intravenous injection, or any combination thereof.

According to some alternative embodiments, the galenic microbial composition is provided in the form of a suppository, such as a vaginal suppository (including a douche, pessary or the like), a rectal suppository, urethral suppository or nasal suppository, or any combination thereof.

According to some embodiments of the multi-component regimen disclosed herein, the acid composition comprises at least one carboxylic acid. In some such embodiments, the carboxylic acid is selected from the group consisting of a straight-chain saturated carboxylic acid (such as propionic acid), a dicarboxylic acid, a tricarboxylic acid (such as citric acid) and any combination thereof.

According to some embodiments, the acid composition has a pH of less than 7, such as for example, in the range of from about 3.5 to less than about 7.

According to some embodiments of the multi-component regimen disclosed herein, the mineral composition comprises minerals selected from the group consisting of sodium, potassium, calcium, magnesium, chloride-containing minerals, sulfate-containing minerals and carbonate-containing minerals. In some such embodiments, the mineral composition comprises magnesium chloride, potassium chloride, sodium chloride, calcium chloride, bromide, sulfate, zinc and water.

According to an exemplary embodiment, the mineral composition comprises 31-35% (w/w) magnesium chloride, 24-26% (w/w) potassium chloride, 4-8% (w/w) sodium chloride, 0.4-0.6% (w/w) calcium chloride, 0.3-0.6% (w/w) bromide, 0.05-0.2% (w/w) sulfate, 0.05-0.3% (w/w) zinc, 34-38% (w/w) water.

According to some embodiments, the minerals of the mineral composition are substantially identical to those present in water of the Dead Sea.

According to some embodiments, the mineral composition further comprises at least one dermatologically compatible film-forming polymer. Non-limiting examples of suitable film-forming polymers include polyvinyl pyrrolidone (PVP), polyvinyl acetate, polyvinyl alcohol (PVA), povidone, hydroxypropyl methyl cellulose (HPMC), ethyl cellulose (EC), hydroxyproplyl cellulose (HPC), chitosan, polymethacrylate copolymer (Eudragit®), polymethylsiloxane, acrylate compolymer, glycols (such as propylene glycols, polyethylene glycols), alcohols (such as ethanol, butanol, isopropanol, benzyl alcohol, lanolin alcohol, fatty alcohols), ethyl acetate, oleic acid, isopropyl myristate.

According to some embodiments, the film-forming polymer comprises polyvinylpyrrolidone. In some such embodiments, the mineral composition comprises minerals, water and polyvinylpyrrolidone. According to an exemplary embodiment, the mineral composition comprises about 35% (w/w) minerals, about 58% (w/w) water and about 7% (w/w) polyvinylpyrrolidone.

According to some embodiments, the film-forming polymer comprises cationic polymers such as cationic polymethacrylate polymers typically comprising copolymers of ethyl acrylate, methyl methacrylate, and a low content of methacrylic acid ester with quaternary ammonium groups (Eudragit® RL and RS). According to some such embodiments, the mineral composition comprises minerals, water and a mixture of Eudragit® RL and RS polymers. In some such embodiments, the mineral composition further comprises an alcohol, such as ethanol and optionally further comprises a plasticizer e.g. glyceryl triacetate (triacetin).

According to a further exemplary embodiment, the mineral composition comprises about 35% (w/w) minerals, about 30% (w/w) water, about 10% (w/w) of a mixture of copolymers of ethyl acrylate, methyl methacrylate and a low content of methacrylic acid ester with quaternary ammonium groups (Eudragit® RL and RS) and about 25% (w/w) of a dermatologically compatible alcohol (such as ethanol).

According to a further exemplary embodiment, the mineral composition comprises about 35% (w/w) minerals, about 30% (w/w) water, about 10% (w/w) of a mixture of copolymers of ethyl acrylate, methyl methacrylate and a low content of methacrylic acid ester with quaternary ammonium groups (Eudragit® RL and RS), about 23% (w/w) ethanol and about 2% (w/w) triacetin.

According to some embodiments of the multi-component regimen disclosed herein, the illuminating and/or heating of the area of the skin of a subject is accomplished using a wearable cutaneous-treatment device suitable for the therapeutic illumination and/or heating of skin, such as mammalian skin (including human or non-human skin).

According to some such embodiments, the wearable cutaneous-treatment device (also referred to herein as a 'wearable device') comprises:
a support component having an inner surface, the support component dimensioned to cover an area of skin of a subject;
at least one light source arranged on the inner surface constituting an illumination panel; and
at least one attachment component for reversibly securing the device to a mammalian subject so that said inner surface faces an area of skin of the subject, the light source or sources configured, when activated, to project light outwards from the inner surface to illuminate at least a portion of the area of skin of the subject.

According to an aspect of some embodiments disclosed herein, there is provided a
wearable device for the therapeutic illumination of skin, such as mammalian skin, the wearable device comprising an illumination panel comprising: a support component having an inner surface, the support component dimensioned to cover an area of skin of a subject;
at least one light source arranged on the inner surface constituting an illumination panel; and
at least one attachment component for reversibly securing the device to a mammalian subject so that said inner surface faces an area of skin of the subject, the light source or sources configured, when activated, to project light outwards from the inner surface to illuminate at least a portion of the area of skin of the subject.

In some embodiments, there is also provided a system and a method for controlling the operation of a wearable cutaneous-treatment device.

According to some embodiments, the support component of the wearable device is contoured or flexible. The support component can be considered the body of the device, primarily serving to hold the single or multiple light sources in a desired manner.

In some embodiments, the support component is rigid but contoured to substantially follow the curves of a portion of a subject's body.

In some embodiments, the support component is flexible. In some exemplary such embodiments, the support component is or comprises a flexible woven cloth or plastic portion in which the plurality light sources are arranged.

In some embodiments, the support component is elastic. In some exemplary such embodiments, the support component is or comprises a flexible elasticized cloth or fabric portion in which the plurality light sources are arranged.

The device according to the teachings herein includes at least one attachment component for reversibly securing the device to a mammalian subject so that the inner surface faces an area of skin of the subject.

In some embodiments, the support component and the attachment component are distinct one from the other, e.g., attachment component comprises reversibly-connectable straps.

In some embodiments, the support component and the attachment component are substantially the same component.

According to some embodiments, the attachment components are elasticized.

Non-limiting examples of suitable attachments or elasticated components include ties, clips, straps, hook and loop fasteners (Velcro®) and the like, or combinations thereof.

According to some embodiments, the illuminating of an area of skin is accomplished by a single light source. According to some such embodiments, the single light source is monochromatic, configured to a single wavelength of light when activated. Any suitable monochromatic light source can be used, e.g., a LED or a laser.

According to some alternative embodiments, the single light source can be polychromatic, configured to emit a plurality of wavelengths of light when activated. Any suitable polychromatic light source can be used, e.g. a filtered tungsten lamp, a xenon lamp, a narrowband LED, an organic LED.

According to some embodiments, the illuminating of an area of skin is accomplished by a plurality of light sources arranged on the inner surface of the support component constituting an illumination panel.

According to some embodiments, a portion or each of the plurality of light sources is monochromatic. According to some such embodiments, the light sources emit light selected from the group consisting of infrared (IR), red, orange, yellow, green, indigo, violet, ultraviolet (UV) and any combination thereof.

In some embodiments, a portion or each of the plurality of light sources is polychromatic.

In some embodiments, the plurality of light sources comprises at least two light sources emitting light of different wavelengths one from the other.

According to some embodiments, at least two of the different types of light sources emit light selected from the group consisting of visible light (i.e. light having a wavelength in the range of from about 400 to about 700 nanometers), ultraviolet (UV) light (i.e. light having a wavelength in the range of from about 10 to about 400 nanometers) and infrared (IR) light (i.e. light having a wavelength of from about 700 nanometers to about 1 millimeter), or any combination thereof.

According to some such embodiments, the visible light is selected from the group consisting of red, orange, yellow, green, blue, indigo or violet light, or a combination thereof. In some such embodiments, the combination provides white light.

According to some embodiments, the ultraviolet light is selected from the group consisting of ultraviolet A, ultraviolet B, ultraviolet C or any combination thereof.

According to some embodiments, the infrared light is selected from the group consisting of infrared A, infrared B, infrared C or any combination thereof.

According to some embodiments, wherein the wearable device comprises at least two different types of light sources, the light sources comprise sources of ultraviolet B, red light, blue light and infrared light.

According to some embodiments wherein the wearable device comprises a plurality of light sources, the light sources are arranged on the inner surface of the support component in a predefined geometric pattern, such as in a circular, triangular or quadratic pattern, a spiral or concentric circles. In some embodiments, the light sources are arranged so that each light that is not at the border of the geometric pattern has four closest neighbors, i.e., rectangular packing. In some embodiments, the light sources are arranged so that each light that is not at the border of the geometric pattern has six closest neighbors, i.e., hexagonal packing.

In some embodiments, the light sources are arranged in a series of rows and columns, such as, for example from 1 to 500 rows and from 1 to 500 columns. In one non-limiting examples, the light sources are arranged as 32 rows with 8 columns.

In some embodiments where the plurality of light sources comprises at least two different types of light sources, each type of light source emitting light different from the other types, the light sources are homogenously distributed on or within the inner surface of the support component so that, when all light sources are activated, the entire area of skin is illuminated with the same light.

Alternatively, in some embodiments where the plurality of light sources comprises at least two different types of light sources, each type of light source emitting light different from the other types, the light sources are heterogeneously distributed on or within the inner surface of the support component so that, when all light sources are activated, different portions of the area of skin am illuminated with different wavelengths of light. For example, in some such embodiments, light sources of a first type are localized in a first part of the inner surface of the support component and light sources of a second type are localized in a second part of the inner surface of the support component so that the device is configured to illuminate a first portion of an area of skin of the subject with light of a first wavelength emitted by the first type of light source and a second portion of an area of skin of the subject with light of a second wavelength emitted by the second type of light source.

In some embodiments, wherein the wearable device comprises light sources providing light of at least two different wavelengths, the wearable device is configured to illuminate a first portion of an area of skin of the subject with light of a first wavelength and a second portion of an area of skin of the subject with light of a second wavelength.

The illumination panel of device according to the teachings herein has any suitable number of light sources, typically any suitable number between 100 and 1000 light sources.

In some embodiments, a device further comprises a power source sufficient to continuously power the light sources to project light for a period of time not less than 15 minutes. In preferred embodiments, the power source is a portable power source, e.g., batteries, so that a subject wearing the device is not forced to remain in a fixed location. In some such embodiments, the portable power source is rechargeable, e.g., comprises rechargeable batteries (e.g., LiION batteries). In some embodiments, such a rechargeable power source is rechargeable using a standard USB or micro USB connector. In some embodiments, the power source is not portable, e.g., the device is powered by the mains power supply.

In some embodiments of the multi-component regimen disclosed herein comprising a step of heating an area of skin of the subject, heating is provided by a device comprising at least one heat source. In some such embodiments, the device is a wearable device. In some such embodiments, the wearable device comprising at least one heat source is a separate device from the wearable device comprising at least one light source.

In some alternative embodiments, at least one light source and at least one heat source are provided in the same wearable device. In some such embodiments, the at least one light source generates sufficient radiant heat to act as at least one combined heat and light source.

In some embodiments, the heat source is configured to, when activated, heat the skin so as to increase the surface temperature of the skin of subject wearing the device to a desired maximum temperature. The maximum temperature is a temperature at which no damage is caused to the skin considering the duration for which the skin-heating component is activated.

The at least one heat source is any one or combination of at least two heat sources. In some embodiments, all heat sources are the same. In some embodiments, at least two heat sources are different.

In preferred embodiments, the heat source or sources are arranged on the inner surface of the support component.

Any suitable type of heat source may be used. In some embodiments, at least one heat source is an infrared heater that is to say, a component which radiates electromagnetic radiation having frequencies in the range of 780 nm to 3000 nm in an intensity sufficient to heat the skin of a subject by radiative heat transfer.

In some embodiments, at least one heat source is a convection heater where a heating element (e.g., a fluid-containing pipe) is heated to heat air, which heated air heats the skin of a subject. In some such embodiments, a heat source comprises a fan to move heated air more efficiently towards a skin surface In some embodiments, power for powering the skin-heating component is provided by the same power source used to power the light sources of the device, as described above.

In some embodiments, a heat source is provided by a non-wearable device.

In some embodiments comprising a wearable device comprising at least one heat source, the device further comprises at least one component selected from the group consisting of a heat sensor configured to monitor the temperature of the area of skin of the subject, a thermostatic control, and combinations thereof.

In some embodiments, such a heat sensor is similar or identical in operation to a non-contact infrared medical thermometer. Typically, such a heat sensor is activated to monitor the surface temperature of an area of skin to be treated.

Additionally or alternatively to a heat sensor as described above, in some embodiments a device includes a thermostat being operatively connected to a heat sensor to measure, for example, skin temperature.

In some embodiments, determination by the heat sensor and/or thermostat that the surface temperature of skin to be treated is below a predetermined lower threshold leads to activation of at least some of the skin heating component to heat the skin. In some embodiments, determination by the heat sensor and/or thermostat that the surface temperature of skin to be treated is above a predetermined intermediate threshold leads to deactivation of at least some of the skin heating component to reduce the rate or extent of heating of the skin. In some embodiments, determination by the heat sensor and/or thermostat that the surface temperature of skin to be treated is above a predetermined upper threshold leads to deactivation of the skin heating component to stop heating of the skin. In some embodiments, activation and/or deactivation of a heat source as a result of determination of skin temperature by the heat sensor or thermostat is by a controller, see below.

In some embodiments, determination by the heat sensor of a temperature below a certain predetermined threshold indicates that the treatment surface is not directed towards the skin, in some such embodiments such determination prevents activation of the light sources. For example, in some embodiments, a temperature below 28° C. indicates that the treatment surface is not directed at the skin so light sources are not activated or deactivated if already activated.

In some embodiments, a device according to the teachings herein further comprises at least one composition application element, configured to provide a predetermined environment to the treated area of a surface of a body of a user during treatment, namely during illumination and/or heating, by application of at least one composition to the surface. For example, the application element or elements, may apply a galenic microbial composition, an acidic composition, a mineral composition or combinations thereof. For example, the application element may apply a composition that renders the treated area acidic. The composition may be in any form known in the art that is suitable for application on the body surface of a subject, for example but not limited to, balm, liquid, gel, spray and the like. The composition application element may be in any form known in the art that renders the composition application element suitable for storage of the composition and application of the composition on the treated area. For example, the composition application element may comprise a container, configured to store the composition; and a composition applicator, configured to apply the composition on the treated area, for example a sprayer, a nozzle, and the like. Another example of a composition application element is a composition-releasing fabric or cloth optionally impregnated or suffused with a composition for application. Said fabric or cloth may be configured as a plaster, comprising a first adhesive site configured to adhere to the skin of a subject, and in some embodiments, a second adhesive side configured to adhere to a protective pouch of the device, see below with referenced to FIG. 1B. Such a composition-releasing release plaster is configured to contain a composition for being applied on the skin of a subject, and release the composition through the first surface once adhered to the skin of the user during use of the device. In some preferred embodiments, the composition is an acidic topical composition, configured to render the treated area of the skin of the subject acidic.

In some embodiments, a device according to the teachings herein comprises a controller for controlling activation and deactivation of other components of the device. Although any suitable controller may be used in implementing such embodiments (e.g., an on-switch with timer that activates the light sources for a predetermined duration), a preferred controller is a computer controller configured with hardware and/or software to accept input from other components of the device or from a user and to output commands to other components of the device or information to a user.

In some such embodiments, the controller is functionally associated with the light sources and is configured to activate or deactivate some or all of the light sources based on predetermined criteria. For example, in some embodiments, the controller is configured to automatically deactivate the light sources a predetermined time after activation of the light sources.

In some such embodiments, the controller is functionally associated with a heating component and is configured to activate or deactivate some or all of the skin heating component based on predetermined criteria.

In some such embodiments, the controller is functionally associated with a heating component and a heat sensor and/or thermostat and is configured to activate or deactivate some or all of the skin heating component based at least in part on input from the heat sensor and/or thermostat.

In some embodiments, the controller comprises a memory. Any suitable memory can be used, such as memory known in the art of computing such as flash memory.

In some embodiments, the controller comprises a memory for storing results received from a heat sensor and/or thermostat.

In some embodiments, the controller comprises a memory for storing one or more treatment profiles as described hereinbelow, and the controller is configured to access a stored treatment profile and then activate and deactivate other components of the device in accordance with the accessed treatment profile.

In some embodiments, the controller comprises a memory that stores one or more treatment profiles, each treatment profile being a specific protocol during which other components of the device, specifically the light sources and, if present, heating component are activated and deactivated according to a predetermined schedule for the duration of the protocol. In some embodiments, the protocol includes activating or deactivating one or more components of the device on receiving some specific reading from a thermostat, heat sensor or similar component.

In some embodiments, the device includes a user interface allowing a human user to input commands to the controller and to receive information from the controller. For example, in some embodiments, the controller is configured to output readings of made by a thermostat, heat sensor or similar component through the user interface. For example, in some embodiments, the controller is configured to accept commands from the user interface, for example, to receive and store a treatment profile input from the user interface.

In some embodiments, a user interface may be used to input to the controller a treatment profile for immediate activation. Any suitable user interface may be used for implementing a device according to the teachings herein.

In some embodiments, a user interface is a graphic-user interface implemented on a display panel, for example, a display screen such as known in the art of smartphones. Accordingly, in some embodiments, a device further comprises display panel in communication with the controller, the display panel configured to display data received from the sensor and/or to receive instructions from a user.

In some embodiments, a user interface comprises a hardware portion that comprises a transmitter (e.g., a radiofrequency transmitter (e.g., Bluetooth®), infrared transmitter) that is physically associated with the controller, and a software portion that is configured to run on a remote device (e.g., a remote control or smartphone of a user). When in use, a user uses the remote device to input commands/receive information which are wirelessly transmitted to and received by the controller via the hardware portion.

In some embodiments a device comprises an alarm, in some preferred embodiments, functionally associated with a processor of the device. Such an alarm is configured to provide an alarm signal relating to the operation of the device and/or of the processor. For example, such an alarm may start when a treatment has been ended, for example in situations when a treatment profile is set for a predetermined duration of time; or when the treatment is stopped prematurely, and the like. Any type of alarm is under the scope of the present subject matter, for example but not limited to, a sound alarm like a buzzer, a visual alarm like a blinking light, an alarm signal sent to the host, and the like.

According to some embodiments, the multi-component regimen, galenic microbial composition or wearable device disclosed herein is for treating a skin condition selected from the group consisting of psoriasis, vitiligo, eczema, acne, dermatitis, lupus, tinea, versicolor, rosacea, actinic keratosis, leukoderma, herpes simplex virus, lupus, a bacterial, viral, fungal or mycobacterial skin infection, a phyto skin infection, a wound, a diabetes-induced skin condition, a skin rash, a pressure sore, a bed sore, a burn, athlete's foot, diaper rash, itching, chafing, or any combination thereof.

According to an aspect of some embodiments of the invention, there is provided a system for the treatment of a skin condition, comprising at least two selected from the group consisting of a galenic microbial composition, an acidic composition, a mineral composition, a source of heat and a source of light.

According to an aspect of some embodiments of the invention, them is provided a kit for the treatment of a skin condition, comprising at least two selected from the group consisting of a galenic microbial composition, an acidic composition, a mineral composition, a source of heat and a source of light.

According to an aspect of some embodiments of the invention, there is provided a combination of at least two compositions selected from the group consisting of:

a galenic microbial composition;
an acidic composition; and
a mineral salt composition,
for use in the treatment of a skin disorder.

According to an aspect of some embodiments of the invention, them is provided the use of a combination of at least two compositions selected from the group consisting of:

a galenic microbial composition;
an acidic composition; and
a mineral salt composition,
in the preparation of a medicament for the treatment of a skin disorder.

Unless otherwise defined, all technical and scientific terms used herein have the same meaning as commonly understood by one of ordinary skill in the art to which the invention pertains. In case of conflict, the specification, including definitions, will take precedence.

As used herein, the term "cutaneous condition" relates to any condition that affects the organ system that encloses the body, including skin, hair, nails, and related muscles and glands. Examples of a cutaneous condition typically include, but are not limited to, medical conditions and cosmetic conditions that are associated with medical conditions. Examples of medical conditions include but are not limited to, psoriasis, vitiligo, eczema, acne, dermatitis, seborrheic dermatitis, atopic dermatitis, actinic keratosis, Urticaria, scleroderma, tinea versicolor, leukoderma and the like. For the sake of simplicity, the term "cutaneous condition" has been used herein interchangeably with the term "skin condition".

As used herein, the term "galenic microbial composition" refers to a composition comprising one or more microorganisms selected from the group consisting of a bacterium, a fungus, a yeast, an alga, a virus, a protozoa, or a product derived from or produced by such a microorganism, and a dermatologically compatible carrier. As used herein, the term "pharmaceutical microbial composition" refers to a formulation comprising one or more microorganisms selected from the group consisting of a bacterium, a fungus, a yeast, an alga, a virus, a protozoa or products derived from such a microorganism, and a medium generally accepted in the art for the delivery of the biologically active compound to mammals, e.g., humans. Such a medium includes all pharmaceutically or cosmetically acceptable carriers, vehicles, diluents or excipients therefor.

As used herein, the term "cosmetic microbial composition" refers to a formulation comprising one or more microorganisms selected from the group consisting of a bacterium, a fungus, a yeast, an alga, a virus, a protozoa or products derived from such microorganisms, and a medium generally accepted in the art for the cosmetic use of a compound in mammals, e.g., humans. Such a medium includes all dermatologically compatible carriers, diluents or excipients therefor.

As used herein, the term "treating" includes ameliorating, mitigating, and reducing the instances of a disease or condition, or the symptoms of a disease or condition. In some embodiments, the treating refers to medical treatment i.e. treatment relating to the health of the subject. In some embodiments, the treating refers to cosmetic treatment i.e. treatment relating to aesthetic, non-medical aspects of a skin condition.

As used herein, the term "administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, intramuscular, intraosseous, intrathecal, and transdermal, or combinations thereof. "Administering" can also include providing a different compound that when ingested or delivered as above will necessarily transform into the compound that is desired to be administered, this type of "different compound" is often being referred to as a "Prodrug". "Administering" can also include prescribing or filling a prescription for a dosage form comprising a particular compound. "Administering" can also include providing directions to carry out a method involving a particular compound or a dosage form comprising the compound or compounds.

As used herein, the term "therapeutically effective amount" means the amount of an active substance that, when administered to a subject for treating a disease, disorder, or other undesirable medical condition, is sufficient to have a beneficial effect with respect to that disease, disorder, or condition. The therapeutically effective amount will vary depending on the chemical identity and formulation form of the active substance, the disease or condition and its severity, and the age, weight, and other relevant characteristics of the patient to be treated. Determining the therapeutically effective amount of a given active substance is within the ordinary skill of the art and typically requires no more than routine experimentation.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise. As used herein, when a numerical value is preceded by the term "about", the term "about" is intended to indicate +/−10% of that value.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Some embodiments of the invention relate to compositions, devices, systems, kits and methods for the treatment of skin conditions such as psoriasis.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

The methods and treatment regimens according to the teachings herein can be performed using any suitable device or combination of devices. In some preferred embodiments, a method or treatment regimen according to the teachings herein is performed using a wearable cutaneous-treatment device for the therapeutic illumination of mammalian skin according to the teachings herein (also called a wearable device). The device is typically configured to be worn by a subject and, while being worn, to illuminate an area of skin of the subject, for example, an area of skin afflicted with a cutaneous condition. As discussed hereinbelow, in some embodiments the device is configured to heat the area of skin, alternatingly or concurrently with the illumination. In some embodiments, the device is configured to sense (e.g., measure, monitor) various parameters of the cutaneous condition. In some embodiments, the device is configured to be used in any setting, for example while performing activities indoors or outdoors for example while watching TV, reading, hiking and the like. According to one embodiment, the wearable device is portable, namely it may be carried by user to any desired place for usage. According to another embodiment, the wearable device is stationary, namely it is configured to stay in place, for example due to its size, or weight, or complexity of structure.

A wearable cutaneous-treatment device for the therapeutic illumination of mammalian skin according to the teachings herein comprises:

a support component having an inner surface, the support component dimensioned to cover an area of skin of a mammalian subject (preferably a human subject);

at least one light source arranged on the inner surface of the support component constituting an illumination panel; and at least one attachment component for reversibly securing the device to a mammalian subject so that the inner surface faces an area of skin of the subject, wherein the light source or sources are configured, when activated, to project light outwards from the inner surface to illuminate at least a portion the area of skin of the mammalian subject.

A person having ordinary skill in the art is able, upon perusal of the description herein is able to manufacture a device according to the teachings herein without resorting to inventive activity using general common knowledge.

Figure 1A:
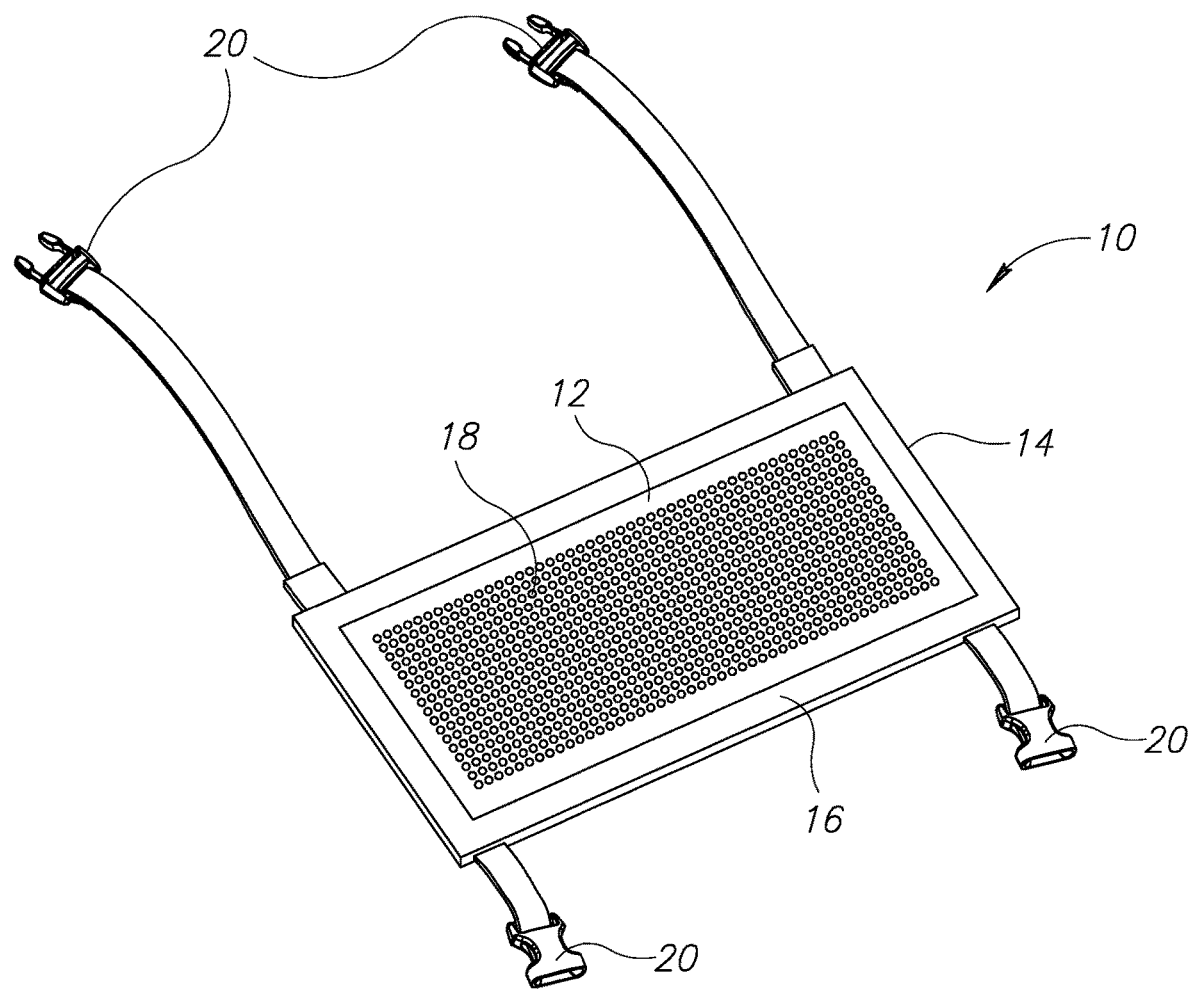
FIG. 1A schematically illustrates, according to an exemplary embodiment, a wearable cutaneous-treatment device viewed towards an illumination panel.

Referring now to the Figures, FIG. 1A schematically illustrates according to an exemplary embodiment, a wearable cutaneous-treatment device 10 viewed towards an illumination panel 12 thereof. Device 10 includes a support component 14 a somewhat flexible pad of multiple layers of woven polyester in which inner surface 16 are arranged 410 light sources (LEDs) 16 which constitutes illumination panel 12. Held inside support component 14 are the required wiring, power supply and controller required of device 10. For light sources 16, device 10 includes 310 UVB and/or NB-UVB LEDs, 20 red LEDs, 20 blue LEDs, 20 green LEDs, 20 white-light LEDs and 20 IR LEDs. The different types of LEDs are distributed homogeneously on illumination panel 12 so that all of an area of skin covered by device 10 when worn is illuminated in substantially the same fashion. As an attachment component, device 10 includes reversibly-closeable attachment straps 20. Device 10 is fashioned to be waterproof, that is to say, can be used when immersed in water, for example, in a shower or swimming pool.

In an alternative, otherwise-identical, embodiment, a device includes an illumination panel having 310 individual LEDS, a total of four different types of light sources of: 160 UVB and/or NB-UVB LEDs illuminating at a central wavelength of 31 nm, 50 red LEDs illuminating at a central wavelength of 633 nm, 50 blue LEDs illuminating at a central wavelength of 415 nm and 50 IR LEDs illuminating at a central wavelength of 830 nm. The different LEDs are distributed homogeneously on the illumination panel.

Figure 1B:
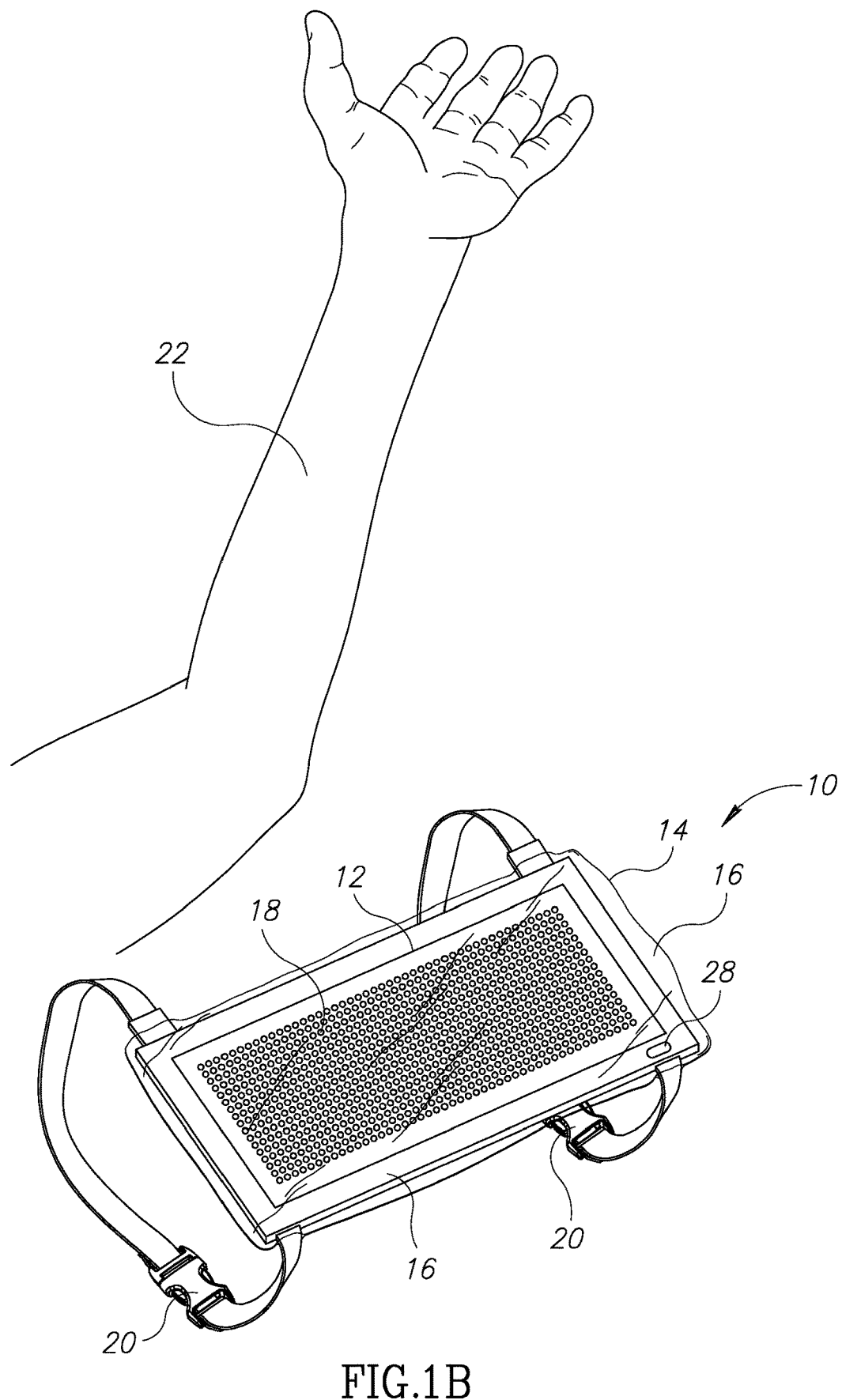
FIG. 1B schematically illustrates, according to an exemplary embodiment, a wearable cutaneous-treatment device viewed towards an illumination panel near an exemplary part of a user's body.

FIG. 1B schematically illustrates device 10 viewed towards illumination panel 12 near an exemplary part of a body of a subject, arm 22. As is understood from FIG. 1B, device 10 is secured to a part of the body of a subject by holding illumination panel 12 against the portion of skin to be treated, securing attachment straps 20 one to the other and then tightening straps 20 to immovably hold device 10 against the body of the subject. In FIG. 1B, support component 14, including inner surface 16 and an outer surface 24 are held inside a protective pouch 26. Pouch 26 protects support component 14 and illumination panel 12, for example, from dirt, dust, humidity and to prevent contact of illumination panel 12 with a topical composition applied on the treated area of a surface of a body of a user, and the like. At least part of pouch 26 that covers illumination panel 12 is sufficiently transparent to the light emitted by light sources 18 of illumination panel 12 so as not to negatively influence the results of the phototherapy treatment applied by illumination panel 12. Thus, pouch 26 is fashioned of any material known in the art that fulfills the aforementioned requirements, for example, is made of plastic sheeting and the like. Also seen in FIG. 1B is switch 28 which is functionally associated with the controller of device 10.

Figure 1C:
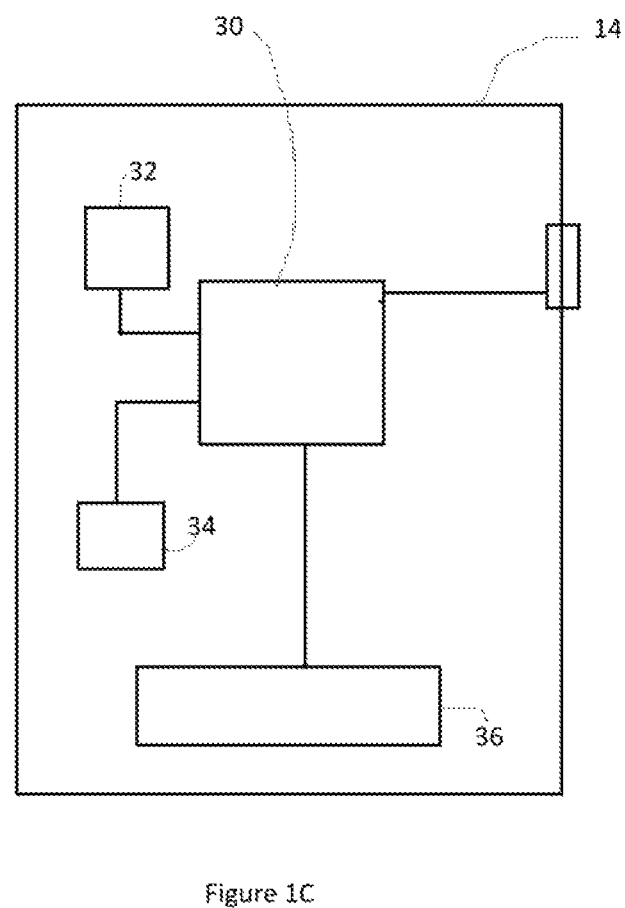
FIG. 1C schematically illustrates, according to an exemplary embodiment, a close-up view of the inside of an illumination panel 12, showing a controller, FIG. 2 schematically illustrates, according to an exemplary embodiment, a close-up view of an illumination panel of a wearable cutaneous-treatment device.

FIG. 1C schematically depicts the inside of support component 14 of device 10 in cross section parallel to illumination panel 12, showing a controller 30 with a memory 32 and a Bluetooth® transceiver 34, a power source 36 and switch 28 embedded inside support component 14. Switch 28 has three states: a first "off" state where none of the components of device 10 receive power and cannot operate, a "manual" state where all the LEDs are activated to illuminate for 15 minutes before shutting down and a "APP" state where controller 30 uses Bluetooth® transceiver 34 to establish and maintain wireless communication with a host (e.g., computer, tablet or smartphone) running control software for the device and, when wireless communication is maintained to receive commands such as to operate and cease to operate from the smartphone.

Figure 2:
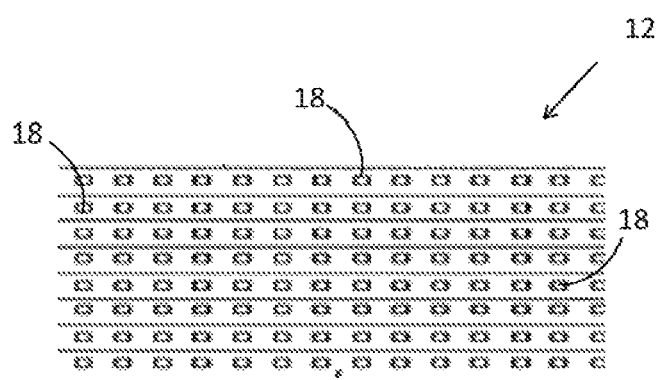

FIG. 2 schematically illustrates a close-up view of a portion of illumination panel 12 of an embodiment of a device according to the teachings herein, showing LEDs 18 arranged in columns and rows.

Figure 3:
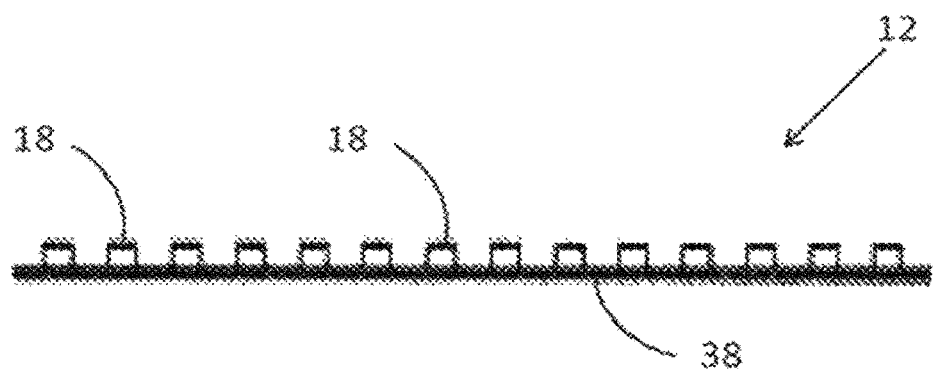
FIG. 3 schematically illustrates, according to an exemplary embodiment, a side view of an illumination panel of a wearable cutaneous-treatment device.

FIG. 3 schematically illustrates a side view of a portion of illumination panel 12 of device 10. Illumination panel 12 comprises a support sheet 38 and a plurality of light sources, LEDs 18 attached to support sheet 38. As noted above, illumination panel 28 is configured to be placed on a surface of a body of a user with light sources 18 facing the surface of the body. For example, illumination panel 12 is placed on an area of a skin where there is a cutaneous condition to be treated by illumination. An exemplary cutaneous condition that may be treated with illumination panel 12 of device 10 is a psoriasis skin lesion.

According to some embodiments, support sheet 38 may comprise a synthetic or natural cloth or fabric, a conductive or non-conductive polymer, or the like.

In some embodiments, the distance between the surface of an illumination panel of a device and a treated area of a surface of a body of a user is fixed, typically between 0 and 3 cm. A non-zero distance can be maintained in any suitable way, for example, pads of material (e.g., rolls of cloth, lengths of silicon rubber) arranged around the periphery of the illumination panel.

In some embodiments, the distance between the surface of an illumination panel and a treated area of a surface of a body of a user is adjustable, typically in the range of between 1 and 3 cm. The distance can be adjusted in any suitable way, for example, inflatable rolls of material (e.g., tubular balloons covered with an elastic-cloth) arranged around the periphery of the illumination panel. Such adjustable distance allows the user to adjust the distance of the illumination panel to the treated area of a body of the user to give rise to optimal treatment results.

In some embodiments, a support sheet such as support sheet 38 is rigid. In some embodiments, a support sheet such as support sheet 38 is flexible, for example made of fabric, nylon sheet and the like, thus allowing the illumination panel to bend to confirm to the shape of the surface of a body on which it is placed.

As noted above, light sources used in implementing a device according to the teachings herein may be any suitable light sources. In preferred embodiments, such as in device 10, the light sources are LEDs (light-emitting diodes) 18.

Figure 4:
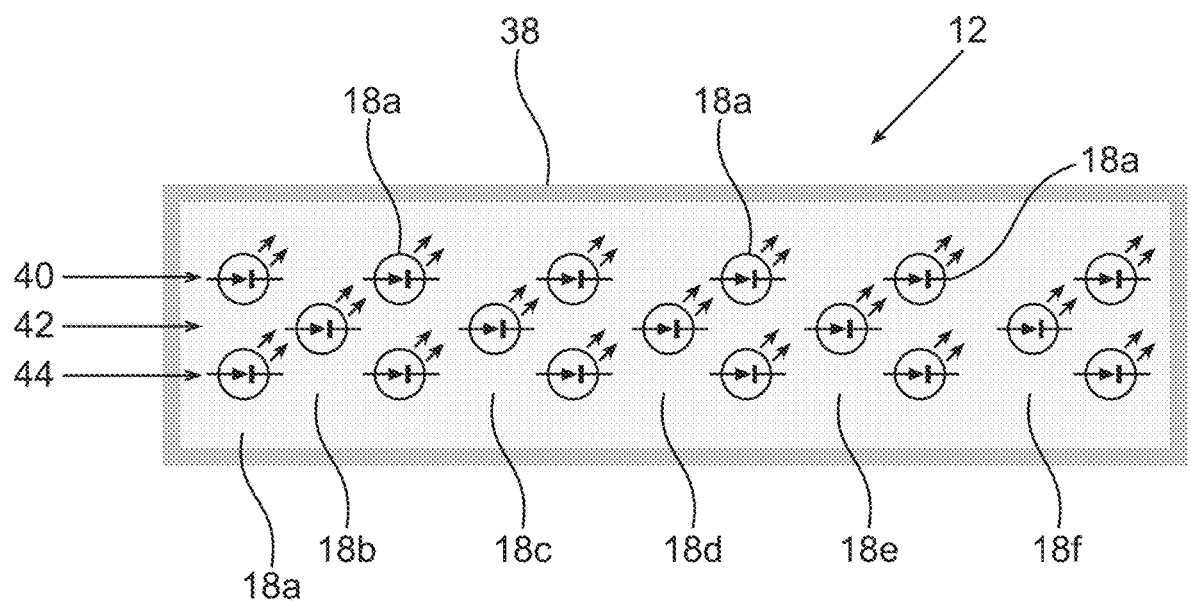
FIG. 4 schematically illustrates, according to an exemplary embodiment, a close-up schematic view of an illumination panel of a wearable cutaneous-treatment device.

FIG. 4 schematically illustrates a close-up schematic view of part of an exemplary embodiment of illumination panel 12 of device 10 arranged in a specific geometric pattern. In some embodiments, all of the light sources are arranged in a regular array. In some embodiments, such as depicted in FIG. 4, the most common type of light sources (the 310 UVB and/or UVB-NB LEDs) are arranged in a regular 31×10 rectangular array) while the less common type of light sources are interspersed within the array. In FIG. 4 are seen part of three rows of light sources, row 40, row 42 and row 44. Rows 40 and 44 include only UVB or UV-NB light sources 18a while row 42 includes a red light source 18b, a blue light source 18c, a green light source 18d, an IR light source 18e and a white light source 18f.

In other embodiments the light sources such as LEDs are arranged in any other suitable pattern, for example, an illumination pattern that mimics irradiation by the sun in the area of the Dead Sea, which is believed by some to be optimal for the treatment of cutaneous conditions—a treatment type so-called Dead Sea climatotherapy.

Furthermore, depending on the embodiment, different wavelengths of light can be emitted from light sources that are configured to emit only one type of light, e.g., monochromatic light sources and/or from light sources that are polychromatic and emit multiple wavelengths of light, e.g. a light source that emits white light such as 18f in FIG. 4 or a light source that is configured to emit either red or blue or green or white light; or any combination thereof.

Light sources used in implementing a device according to the teachings herein are any type of suitable light source known in the art. According to one embodiment, the light sources comprise or are LEDs, as depicted in FIGS. 1-4. In such embodiments, any suitable type of LED may be used including suitable LEDS known in the art, for example but not limited to, LEDs that are based on AlGaN, AlGaP, GaAlAs, InGaN/GaN, AlN semiconductors, and the like, generating light within various light wavelength ranges.

It should be noted that an illumination panel of a device according to the teachings herein may be of any suitable size and/or dimensions and/or shape that are suitable for covering an area of a surface of a body of a subject to be treated. Thus, any size and/or any dimensions and/or any shape of the illumination panel are within the scope of the present subject matter. For example, in some embodiments and illumination panel is rectangular, circular, oval, and the like, at any size or dimensions. Further, any suitable number of light sources, including more than 1,000 light sources, is within the scope of the present subject matter, as the size, dimensions and shape of the illumination panel 10 may allow.

Figure 5:
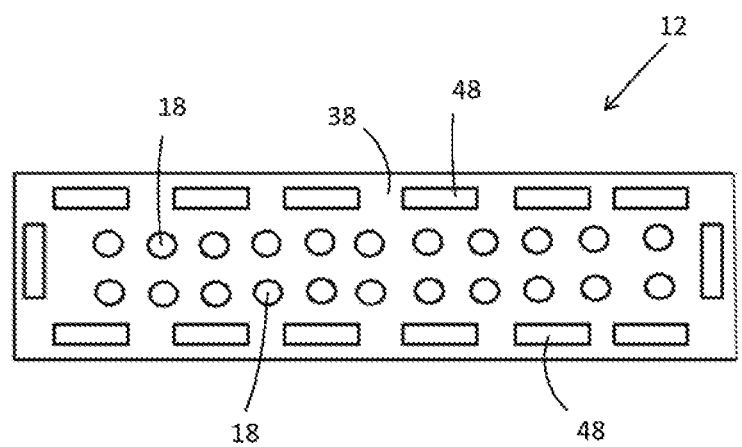
FIG. 5 schematically illustrates, according to an exemplary embodiment, a view of an illumination panel of a wearable cutaneous-treatment device comprising a plurality of light sources and a plurality of heating pads.

As noted above, in some embodiments a device according to the teachings herein comprises a skin heating component. In some embodiments, the skin heating component is at least partially found on the inner surface of the support component, the illumination panel. FIG. 5 schematically illustrates a view of an exemplary embodiment of an alternative illumination panel 46 of device 10 according to the teachings herein, comprising a plurality of light sources 18 and a plurality (fourteen) of individual heating pads 48 comprising a heat resistive material printed on a support sheet 38, wherein heating pads 48 emit heat upon passage of an electric current, which together constitute a skin heating component of device 10. In device 10, illumination panel 46 includes a support sheet 38 to which are attached light sources 18 and heating pads 48.

In some embodiments a device is configured to optionally function in a mode where only the heating component is activated to heat the skin surface and the light sources are not activated to illuminate the skin surface.

Additionally or alternatively, in some embodiments a device is configured to optionally function in a mode where only the light sources are activated to illuminate the skin surface and the heating component is not activated to heat the skin surface.

Additionally or alternatively, in some embodiments a device is configured to optionally function in a mode where both the light sources are activated to illuminate the skin surface and the heating component is activated to heat the skin surface.

In some embodiments there is no separate heating component and rather some or all of the light sources, when operated, produce sufficient heat to effectively function as a heating component of a device. In some such embodiments, a device further comprises a heat-dispersion mechanism (preferably associated with the illumination panel) configured to homogenously disperse the heat generated by the light sources throughout the illumination panel and over the treated area of a surface of a body of a subject. In some such embodiments, a device further comprises a heat-dispersion mechanism (preferably associated with the illumination panel) as a means for heating a treated area of a surface of a body of a subject.

In some embodiments, a device comprises a separate heating component (preferably associated with the illumination panel, such as heating pads 48 of device 52 in FIG. 5) and a heat dispersion mechanism as described immediately hereinabove, that may be operated separately or simultaneously for heating the treated area of a surface of a body of a subject.

In some embodiments, a device according to the teachings herein further comprises at least one sensor. In such embodiments, the at least one sensor is configured to monitor the condition of a treated area of a surface of a body of a user, for example in order to monitor the condition of the treated area prior the treatment in order to allow application of a type of treatment that is suitable for the condition of the area to be treated. The at least one sensor may be used also for monitoring the condition of the treated area during or after treatment in order to aid in the assessment of the results and progress of the treatment.

Any type of sensor known in the art that is suitable for monitoring the condition of a treated area of a surface of a body of a user is under the scope of the present subject matter. Examples of such a sensor include, but not limited to: at least one heat sensor (also called temperature sensor), configured to monitor the temperature of the treated area during treatment, for example in order to prevent overheating of the treated area, as discussed above. The at least one sensor may be attached to the illumination panel (e.g., to a support sheet that is part of the illumination panel) or is physically separate from the illumination panel, or any combination thereof.

Figure 6:
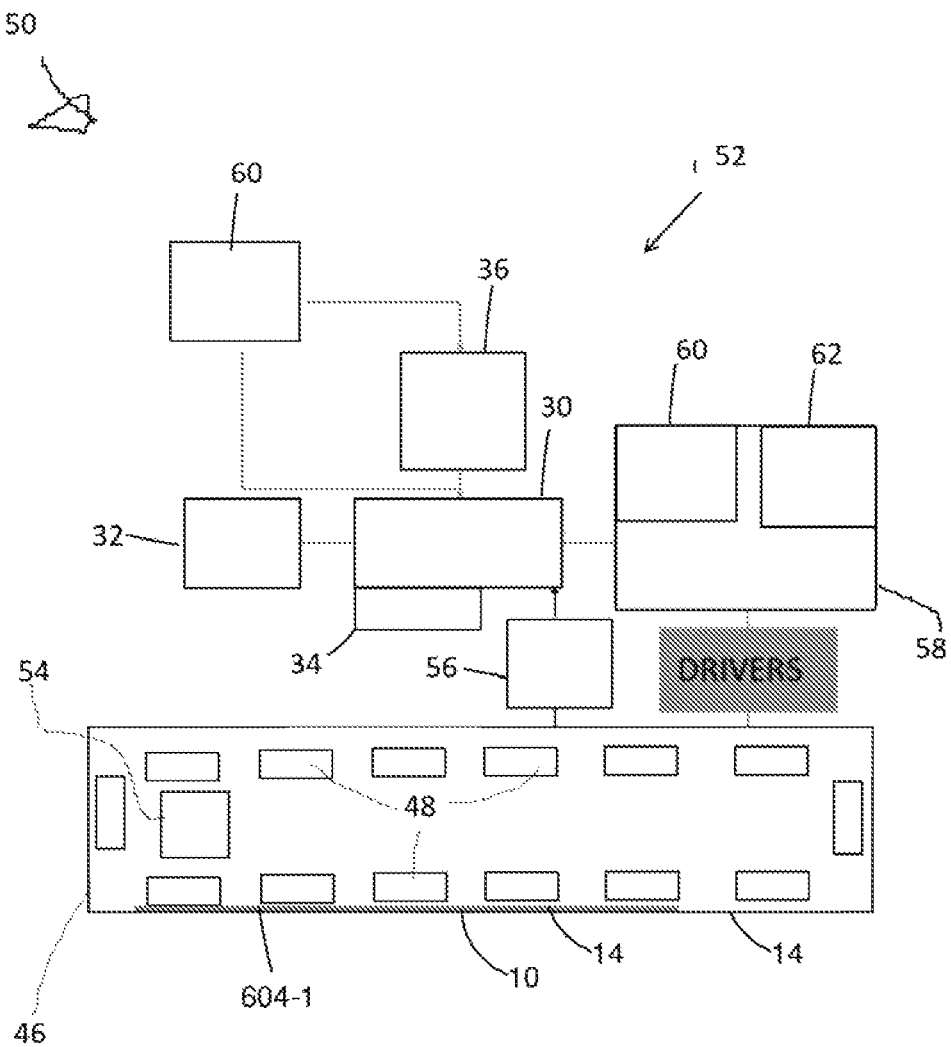
FIG. 6 schematically illustrates, according to an exemplary embodiment, a block diagram of a system for controlling the operation of a wearable cutaneous-treatment device.

The present subject matter further provides a system for controlling the operation of a wearable cutaneous-treatment device. FIG. 6 schematically illustrates, according to an exemplary embodiment, a block diagram of a system 50 for controlling the operation of an embodiment of wearable cutaneous-treatment device 52 having an illumination panel 46 as described with reference to FIG. 5. Device 52 is substantially similar to device 10 described above.

System 50 comprises a controller 30. Controller 30 is communicationally connected to illumination panel 46 and is configured to control the operation of the light sources (not depicted in FIG. 6) thereof as well as to control the operation of heating pads 48 constituting the heating component of device 52, as well as to receive data from at least one sensor, for example a light board temperature sensor 54 configured to determine the temperature of illumination panel 46, and a skin temperature sensor 56, configured to determine the temperature of an area of a surface of a body of a user that is treated with device 52.

System 50 further comprise a control panel 58 with a display 60 (e.g., LCD or LED display) communicationally-connected to controller 30 configured to display data regarding the operation of device 52, such as data received from at least one of sensors 54 and 56, and the like. In some embodiments, a display is a component of a device, for example display 58 of device 52. In some alternate embodiments, a display is a display of a remote device (e.g., a smartphone) in communication with a controller of a device.

Control panel 58 of system 50 further comprises a keyboard 62 as an input component connected to controller 30 to input user commands and data for operating device 52. In some alternate embodiments, an input component is an input component of a remote device (e.g., a smartphone) in communication with a controller of a device. Drivers 64 provide power to the light sources.

System 50 further comprises a memory 32 communicationally connected to controller 30. Memory 32 is configured to store, for example, predetermined treatment profiles, i.e., predetermined patterns (protocols) of illumination and/or heating of an area of a surface of a body of a subject. A treatment profile may comprise illumination/heating duration parameters, intensity parameters of the illumination/heating, changing patterns of wavelength and/or temperatures and/or duration of illumination/heating in each type of light/temperature, frequency of pulsation of light irradiation and/or heating, and the like. A treatment profile may also comprise information about the type of cutaneous condition that the treatment profile is suitable to treat.

System 50 further comprise a host 60 communicationally connected to controller 30. Host 60 is a computing device, for example, but not limited to, a computer, a smartphone, a mobile phone, a tablet, and the like. According to one embodiment, host 60 is configured to operate and/or store software, for example computer programs or smartphone applications, for the operation of device 52. In some embodiments, host 60 is configured to display data received by at least one of sensors 54 and 56, or data provided by a user, as described hereinafter. Alternately or additionally, in some embodiments a host is configured to process images. According to a further embodiment, a host is configured to collect data, analyzed the collected data and export data relating to treatment regimes.

System 50 is configured to automatically shut down when there is a need for system 50 to shut down, for example, when a treatment has been ended, when device 52 is overheated, the when safety of the user is at risk, and the like.

System 50 further comprises a power source 36, as described above, for example a battery, electrically connected to the components of the system 50 for supplying electrical power for their operation.

In some embodiments, a system of a device further comprises a user manual, detailing instructions for use, troubleshooting and any other information needed for safe and efficient operation of the wearable device and the system.

The various components of system 50 are communicationally connected by any type of communication connection known in the art, for example but not limited to, wired communication like a cable with USB plugs, unwired communication like Bluetooth®, Wifi, and the like. In FIG. 6, system 50 comprises a Bluetooth® transceiver 34 functionally associated with controller 30 that enables communication between the controller 30 and other components of system 50, for example host 66.

As noted above, treatment of a skin surface of a subject with a device according to the teachings typically comprises a treatment profile which includes a light and/or heat treatment of a cutaneous condition. The illumination pattern, namely the wavelengths and doses and duration of illumination, of the light emitted from various light sources, as well as the heating pattern, may be controlled, either manually or automatically. A treatment profile may be provided, based for example on updated results of research conducted in the area of treatment of cutaneous conditions with light and heat. A specific treatment profile may be based on various parameters, for example, but not limited to, skin type, physician's recommended treatment, age, gender, type of cutaneous condition, severity of the cutaneous condition, and the like.

In some embodiments, a system is configured to provide various types of treatment profile, as well as create new treatment profiles based, for example on data about a user and/or a cutaneous condition provided to the system, or data based on scientific research on cutaneous conditions treatment provided to the system. The system is capable of allowing the creation of treatment profiles comprising a wide range of spectral light exposure, various types of heating treatments, various treatment duration times, various pulsating of illumination types, and any combination thereof. Furthermore, the operation of a device and of a system may be conducted in accordance with established safety procedures and regulations.

Controller 30 of system 50 is communicationally connected to the illumination panel 46, and is configured to control the operation of illumination panel 46, including illuminating, heating or concurrently illuminating and heating of an area of a surface of a body of a subject.

In some embodiments, controller 30 controls the operation of illumination panel 46 using predetermined treatment profiles, which are stored in memory 32 that is communicationally connected to controller 30. In addition, controller 30 is communicationally-connected to host 66, for example a computer, a smartphone, a mobile phone, a tablet, and the like. A user may use host 66 to operate controller 30, which in turn activates a treatment profile according to the choice of the user.

In some embodiments, a device according to the teachings herein may be activated manually. In other words, a user may select a predetermined treatment profile manually, for example by using keyboard 62 which is physically associated with device 52 or by using host 66, for example by using a keyboard of a computer or a touch-screen of a smartphone or a tablet.

Once a treatment profile is selected it may be activated, and as a result the illumination panel illuminates, or heats, or concurrently both illuminates and heats an area to be treated according to the chosen treatment profile.

In some embodiments, a system associated with a device according to the teachings herein is configured to store and run software that is configured to diagnose the situation of a cutaneous condition of a subject, by analyzing data provided, for example, by a user, a professional person like a physician, and the like. Any type of data analysis that is performed by the software is under the scope of the present subject matter. Any type of data known in the art is under the scope of the present subject matter. Examples of data include, but not limited to, text, images and the like. For example, text data may be answers to a questionnaire regarding a user and the condition of a cutaneous condition to be treated, images of hair, eyes and the like. Any type of image known in the art is under the scope of the present subject matter. Furthermore, the image may be of any subject known in the art that may be used during analysis for the determination of the situation of a cutaneous condition of a user. Image data may be images of a cutaneous condition to be treated. Data that are provided to the software may be stored in a memory for future usage, for example for monitoring the progress of treatment of a user, research analysis of the data, and the like.

The software is configured to analyze the data and accordingly provide a treatment profile for treating a cutaneous condition. According to one embodiment, the software may either choose a predetermined treatment profile, or design a new treatment profile, that corresponds to the diagnosis and is expected to yield optimal treatment results. According to an additional embodiment, the software is configured to be updated with results of research in the area of treatment of cutaneous conditions, based for example on the most updated research, so it may activate the most updated treatment profiles, for the benefit of the user. According to some embodiments, the software may be stored in, an operated by, a host such as host 66, namely a computer, a smartphone, a mobile phone, a tablet, and the like.

For example, the software may diagnose the cutaneous condition of a user according to the Fitzpatrick skin type classification scale, and provide a treatment profile suitable for the type of cutaneous condition that was diagnosed. Table 1 summarizes some UVB light treatment profiles that are suitable for different types of cutaneous conditions according to the Fitzpatrick skin type classification scale.

TABLE 1

| Skin Type | Start dose [mJ/cm$^2$] | 2$^{nd}$ dose [mJ/cm$^2$] | 3rd dose [mJ/cm$^2$] | 4$^{th}$ dose [mJ/cm$^2$] | subsequent increments |
|---|---|---|---|---|---|
| I | 100 | 140 | 180 | 220 | 20% of previous dose |
| II | 120 | 170 | 220 | 270 | 20% of previous dose |
| III | 150 | 210 | 270 | 330 | 20% of previous dose |
| IV | 200 | 280 | 360 | 440 | 20% of previous dose |
| V | 300 | 420 | 540 | 600 | 20% of previous dose |
| VI | 500 | 700 | 900 | 1100 | 20% of previous dose |

* Maximum single dose 5000 mJ/cm$^2$

Figure 7:
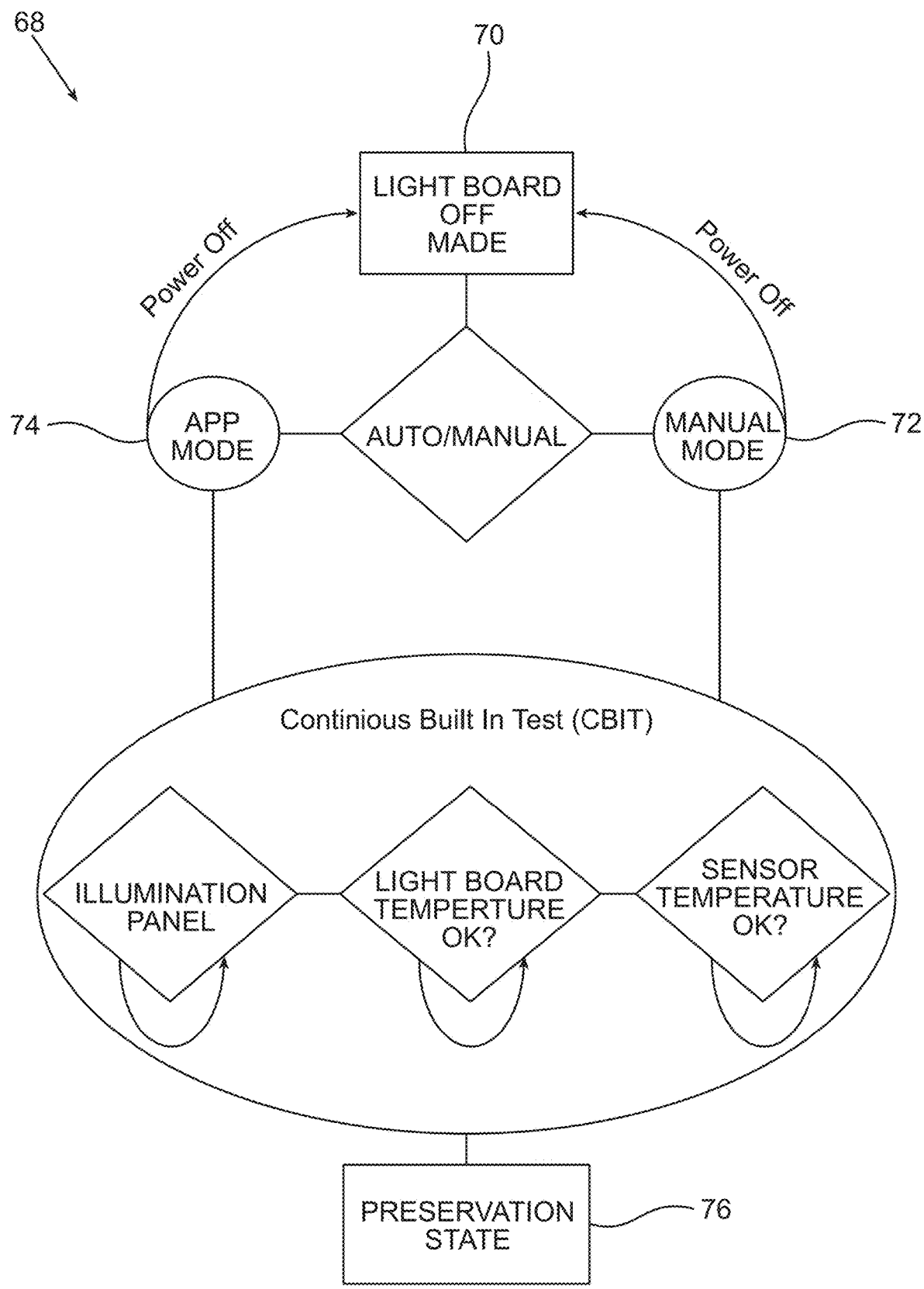
FIG. 7 schematically illustrates, according to an exemplary embodiment, a block diagram of states and modes of operation of the system for controlling the operation of a wearable cutaneous-treatment device.

FIG. 7 schematically illustrates, according to an exemplary embodiment, a block diagram 68 of states and modes of operation of the system for controlling the operation of a device 52 provided with a system 50 as depicted in FIG. 6.

In Off Mode 70, device 52 is connected to power source 36 and power source 36 is charged to a sufficient level. Device 52 is not connected to host 66 and illumination panel 46 is not functioning.

For operation, in 72 a user uses a switch to activate device 52. The switch used is optionally a dedicated switch and/or a switch implemented via keyboard 62 of control panel 58. In some embodiments, immediately after device is activated 72 a user selects either Manual Mode 74 or APP Mode 76. In some embodiments, during activation either Manual Mode 74 or APP Mode 76 is selected, e.g., a switch is a three-state switch (Off/Manual/App) especially a three-state toggle switch.

In Manual Mode 74, a user may select, via keyboard 62 and display 60 of control panel 58, to revert 78 to Off Mode 70 or to select a desired treatment profile, namely determine for example illumination intensity and treatment duration. During Manual Mode 72, Bluetooth® transceiver 34 is disabled. After user-selection of operational parameters, it is confirmed that device 52 is placed on a treatment area of the body of the subject, and a "StartTreatment" option is selected using control panel 58. The initial activation of the light sources of illumination panel 46 may be done gradually, and only after the skin temperature sensor 56 show that illumination panel 46 is positioned over the skin. Skin temperature sensor 56 measure initial skin temperature should be in the range of substantially 28-34° C. If the measured skin temperature is below this range, the operation of the light sources of illumination panel 46 is stopped.

In APP Mode 76, a user may select to revert 78 to Off Mode 70, but ordinarily Bluetooth® transceiver 34 is activated and waits for establishing communication with host 66. After communication is established, software, for example an application, stored for example on host 66, is activated and controls the operation of device 52. This may be achieved for example by initiation of communication between host 66 and controller 30 of device 52. Once communication has been established, a treatment profile is set. Periodically, for example every three seconds, device 52 sends a status message to host 66. This periodic message is used for information purpose for a user, or stored in log. The operation of device 52—for example, control of electric current supplied to the light sources, control of illumination panel temperature and skin temperature, timing and any safety issues, is done by controller 30.

During both Manual Mode 74 and App Mode 76, a Continuous Built in Test Unit 80 of controller 30 monitors various parameters that relate to the operation of device 52. If Test Unit 80 detects an exceptional parameter, device 52 is automatically changed to Preservation Mode 82, optionally while activating an alarm and/or reporting the reason for entering Preservation Mode 82 on display 60 of control panel 58.

In Preservation Mode 82, illumination panel 46 is not powered and not functioning, but communication between device 52 and host 66 is maintained (if in APP Mode). Device 52 may enter into Preservation State 76 in case at least one of the following situations occurs:

skin temperature sensor 56 measures a temperature higher than a predetermined
upper threshold, for example substantially 45° C.;
skin temperature sensor 56 measure a temperature lower than a predetermined lower threshold, for example substantially 26° C., a situation showing that illumination panel 46 may not positioned correctly on the skin and that there is a danger of the subject looking at the light sources so it is important to shut-off illumination panel 46;
light board temperature sensor 54 measures a temperature higher than a predetermined threshold, for example a temperature that may harm illumination panel 46 and/or the user;
the electrical current (e.g., in Amperes) to the light sources is above a predetermined threshold, in order to avoid damage to the light sources.

Figures 8A, 8B:
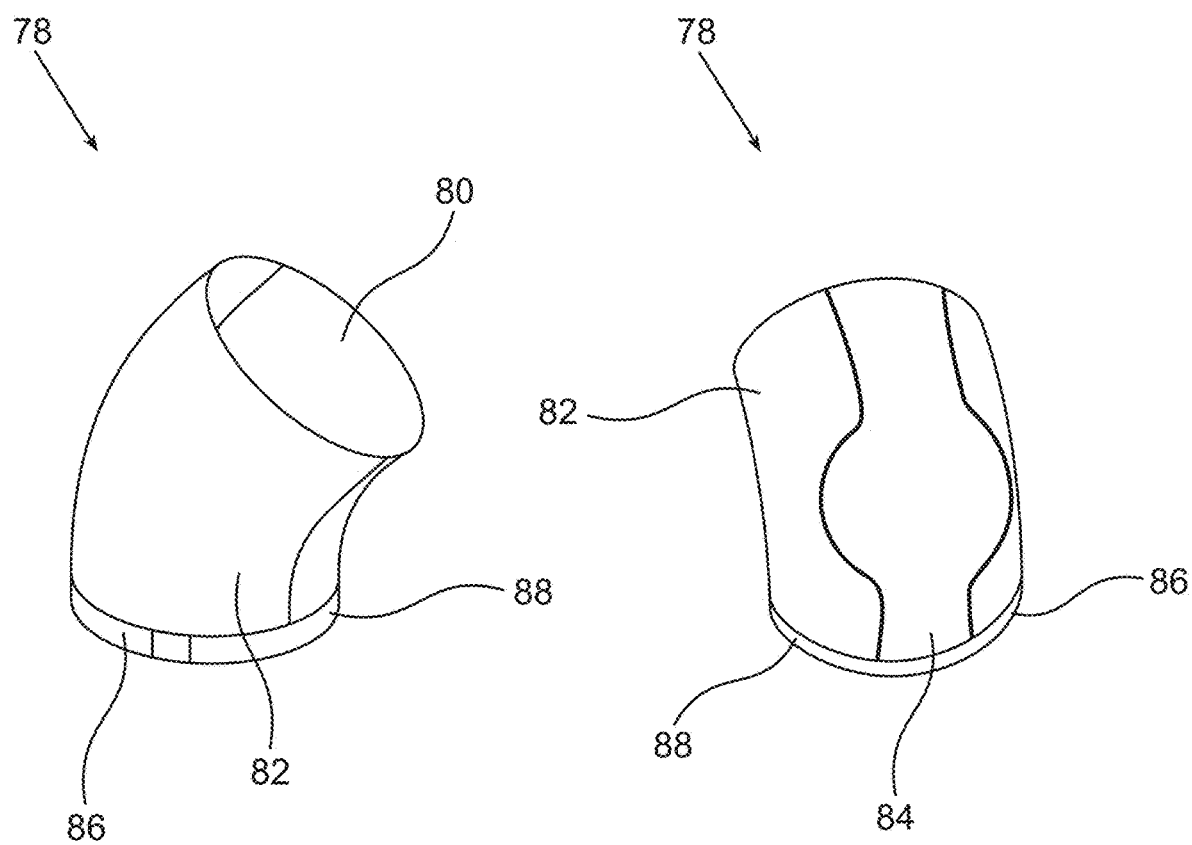
FIGS. 8A and 8B schematically illustrates, according to an exemplary embodiment, a wearable cutaneous-treatment device formed as a sleeve.

In FIGS. 8A and 8B an additional embodiment of a wearable cutaneous-treatment device 84 according to the teachings herein is depicted. In FIG. 8A looking at an illumination panel 80 of device 84 and in FIG. 8B at device 84 from the front.

In device 84, a support component and attachment component are the same component 86, a flexible sleeve made of an elasticized cloth, shaped and dimension to fit over the knee of a human subject.

The entire inner surface of device 84 constitutes illumination panel 88, in which a plurality of light sources (LEDs, depicted as dots in FIG. 8A) is arranged.

Helping to maintain the shape of device 84 is a bendable rib 90 of polyethylene that also functions to protect the knee of a wearer from impact.

A control unit 92 including a controller, memory, power source and also a Bluetooth® transceiver to transmit information and receive commands from software that is loaded on the smartphone or a remote control of the user is attached to the bottom of the device on an encircling band 94.

Examples of Compositions for Use in the Methods Disclosed Herein

I. Exemplary Compositions

Materials

*P. shermanii* bacteria (Propinobacterium 50) were obtained as a freeze-dried bacterial powder from Biena, Canada.

Olive oil (*Olea Europaea* Fruit Oil) was obtained from Sophim, France (CAS No. 8001-25-0).

Tocopherol was obtained from Phyto Active Plant Extracts, Israel (CAS No. 59029) Geranium oil (Pelargonium Graveolens oil) was obtained from Phyto Active Plant Extracts, Israel (CAS No. 8000462)

Rose flower oil (Rosa damascena extract) was obtained from Phyto Active Plant Extracts, Israel (CAS No. 8007010).

Example 1: Bacterial Composition a (Test Composition)

Bacteria:
6.7% (w/w) *P. shermanii* ($1\times10^6$ CCFU, 0.005-2 g freeze-dried mix powder)
Carrier:
92.8% (w/w) olive oil;
0.5% (w/w) tocopherol;
0.01% (w/w) geranium oil; and
0.005% (w/w) rose flower oil.

All carrier ingredients were added to a mixing container and mixed for 5 minutes. The mixture was divided into 90 ml portions and filled into bottles. The bacterial powder was added to each bottle. The bottles were sealed and labelled.

Example 2: Bacterial Composition B

Bacteria:
Brevibacterium sp.; Propionibacteriaacnes; and Micrococcus luteus ($1\times10^6$ CCFU, 0.5-1 g freeze-dried mix powder)
Carrier:
50% (w/w) olive oil;
33.3% (w/w) shea butter,
16.7% (w/w) beeswax.

All carrier ingredients were added to a mixing container and mixed while melting by heating. The temperature of the mixture was adjusted to 45° C. or less. The bacterial powder was added and mixed.

Example 3: Bacterial Composition C

Bacteria:
P. shermanii ($1\times10^6$ CCFU, 0.005-2 g freeze-dried mix powder)
Carrier:
50% (w/w) olive oil;
33.3% (w/w) shea butter,
16.7% (w/w) beeswax.

All carrier ingredients were added to a mixing container and mixed while melting by heating to a temperature of about 65° C.. The temperature of the mixture was then adjusted to 45° C. or less. The bacterial powder was added and mixed.

Example 4: Bacterial Composition D

Bacteria:
Brevibacterium sp.; Propionibacteriaacnes; and Micrococcus luteus ($1\times10^6$ CCFU, 0.5-1 g freeze-dried mix powder)
Carrier:
50% (w/w) olive oil;
12.5% (w/w) pomegranate oil;
37.5% (w/w) rosehip oil.

All carrier ingredients were added to a mixing container and mixed. The bacterial powder was added and mixed.

Example 5: Bacterial Composition E

Bacteria:
6% P. shermanii ($1\times10^6$ CCFU, 0.005-2 g freeze-dried mix powder)
Carrier:
72% (w/w) Aloe Barbadensis leaf juice with water,
2% (w/w) sclerotium gum;
0.2% (w/w) salicylic acid or citric acid;
1.1% (w/w) sodium gluconate;
5% (w//w) saccharide isomerate and/or cetearyl wheat straw;
5% (w/w) glucoside and/or cetearyl;
3% (w/w) coconut oil;
2% (w/w) cetyl alcohol;
3% (w/w) olea Europaea fruit oil;
0.55 (w/w) tocopherol;
0.1% (w/w) Lavendula Angustifolia;
0.1% (w/w) Rosa damscena extract.

Water and aloe Barbadensis leaf juice were mixed in a mixing container and heated to 60° C.

Sclerotium gum, salicylic acid/citric acid, sodium gluconate and saccharide isomerate/cetearyl wheat straw were added to the mixing container and mixed for a further 5 minutes.

In a second mixing container, glucosides/cetearyl, coconut oil, cetyl alcohol and olea Eruopaea fruit oil were mixed and heated to 60° C.

The mixtures in the two mixing containers were slowly combined and mixed for 30 minutes while cooling.

When the combined mixture reached a temperature of less than 40° C., the bacteria, tocopherol, Lavedula Angustifolia and Rosa damascena extract were added and the final mixture further cooled to 25° C.

pH and viscosity were measured and adjusted, and pH adjusted, if necessary, to about 4.5.

Example 6: Acidic Composition 0.1-0.3 mM citric acid in water.

Citric acid was diluted in water and the pH checked to ensure that a value of less than about 7 was attained.

Example 7: Mineral Composition

30% (w/w) Dead Sea minerals in water.
Mineral composition:
31-35% magnesium chloride
24-26% potassium chloride
4-8% sodium chloride
0.4-0.6% calcium chloride
0.3-0.6% bromide
0.05-0.2% sulfate
Water of crystallization, typically 34-38%

The minerals were combined with water and mixed at ambient temperature.

I. Clinical Study Using Bacterial Composition A

Materials and Methods

Subjects 16 otherwise healthy male and female subjects, between the ages of 18-65, suffering from psoriasis vulgaris as diagnosed by a qualified dermatologist and having Phototype I-IV on Fitzpatrick scale were recruited.

Pregnant or breastfeeding women; women planning a pregnancy during the study period; subjects having a history of drug or sun hypersensitivity, recurrent dermatological diseases or recent sunburn; subjects who used topical or systemic treatment during the weeks preceding the study, which were considered liable to interfere with the assessment of the tolerance of the test products; subjects enrolled in another study during the study period; and subjects considered by the investigator to be unlikely to be compliant to the protocol were excluded.

Methods

The purpose of the study was to investigate skin tolerance and efficacy of the test composition in the treatment of psoriasis.

The study was conducted in accordance with the guidelines for Good Clinical Practice defined by the ICH Topic E6 "Notes for Guidance and Good Clinical Practice" (CPMP/ICH/135/95), the Helsinki Declaration (1964, WMA) and its successive updates.

The scope of tests was compliant with Regulation of the European Parliament and of the Council (EC) No. 1223/2009 of 30 Nov. 2009 on cosmetic products; Cosmetics Europe—The Personal Care Association Guidelines "Product Test Guidelines for the Assessment of Human Skin Compatibility 1997"; and Cosmetics Europe—The Personal Care Association Guidelines for the Evaluation of the Efficacy of Cosmetic Products 2008.

Information regarding the study was provided orally and in writing to each participating subject and a written consent form was signed by each subject prior to commencement of the study.

Each subject was initially provided with a bottle comprising 90 ml of the test composition. The subject was instructed to shake the bottle well and then to apply the test composition to skin areas in which psoriasis was present morning and evening a daily over a period of 16 consecutive weeks. The subject was instructed to record the number of applications amount of composition used in a daily log, together with a record of any other medications taken on that day.

Skin condition was assessed by a technician prior to commencement of the study, weekly during the study and after 112 days of use. During each weekly visit, the skin areas under investigation were photographed.

a. Physical Indicators of Skin Condition

Skin condition was further assessed by a dermatologist, before and after application of the product, using a 4 point structured scale to identify specified physical signs of skin reaction, including redness, swelling, dryness, etc., where 0 indicates absence of the physical sign of psoriasis, 1 indicates mild occurrence, 2 indicates moderate occurrence and 3 indicates severe occurrence.

b. Functional Signs of Skin Condition

The subjects were instructed to record functional signs of skin reaction, including burning sensation, tightness, etc., according to the 4 point structured scale as described above. Functional signs were further recorded by a clinical investigator during the monthly visit of each patient.

c. Dermatology Life Quality Index (DLQI)

At the beginning and end of the study (weeks 0 and 16), subjects were further required to fill out a 10 question Dermatology Life Quality Index (DLQI) questionnaire, used to measure the impact of skin diseases on the quality of life of the affected subjects and the DLQI score was calculated.

The scoring of each question was as follows:

| Response | Score |
| --- | --- |
| Very much | Score 3 |
| A lot | Score 2 |
| A little | Score 1 |
| Not at all | Score 0 |
| Not relevant | |
| Question unanswered | |
| Question 7 | Score 3 |

The DLQI was calculated by summing the score for each question, resulting in a maximum score of 30 and a minimum score of 0. A higher score is indicative of a greater degree of impairment of quality of life.

d. Psoriasis Area Severity Index (PASI)

Severity of psoriasis was determined by a dermatologist, according to the Psoriasis Area Severity Index (PASI). The body of each subject was considered to comprise four sections: head (10% of a subject's skin); arms (20%); trunk (30%); and legs (40%). Each section was first scored separately and the scores then combined into a final PASI score. For each section, the percentage of skin involved was estimated and then transformed into a grade from 0 to 6, according to the following:

0: 0% of skin;
1: <10% of skin;
2: 10-29% of skin;
3: 30-49% of skin;
4: 50-69% of skin;
5: 70-89% of skin;
6: 90-100% of skin.

For each section, the severity was estimated by three clinical signs (erythema, induration and desquamation), with severity parameters on a scale of 0 to 4, where 0 indicates no signs and 4 indicates maximum signs. The sum of all three clinical signs was calculated for the skin of each section of the body, multiplied by the percentage of skin involved for that area, and multiplied by the weight of the area score for that section (0.1 for head; 0.2 for arms; 0.3 for trunk; and 0.4 for legs).

Test Schedule

Day 0: The test area was examined by a dermatologist and PASI scores determined.

The test area was photographed.

Weekly (weeks 1-3, 5-7, 9-11 and 13-15): The subjects reported to the study center without having applied any product to the test area. The test area was examined by a technician and photographed. The subjects were instructed to apply the product later in the day after the examination and as usual on the same evening.

Monthly (weeks 4, 8, 12 and 16): The subjects reported to the study center without having applied any product to the test area. The test area was examined by a dermatologist and photographed. PASI scores were determined.

Statistical Analysis

The results were statistically analyzed using the STATISTICA 13® analytics software package (TIBCO Software Inc., USA).

Paired sample-test or two-sided Wilcoxon signed rank sum tests were used to assess differences in results. The level of significance was sent as $p<0.05$.

Post-Study Follow Up

Follow-up was conducted over a 6 month period following completion of the study. Subjects were required to continue the daily log of and to visit the test center on a monthly basis, at which time photo documentation of the condition of the skin area tested was obtained by technicians.

Results a. Dermatology Life Quality Index (DLQI) at weeks 0 and 16.

TABLE 2

| Subject's no. | DLQI scores (W 0) | Meaning of DLQI Scores | DLQI scores (W 16) | Meaning of DLQI Scores |
| --- | --- | --- | --- | --- |
| 1. | 12 | very large effect on subject's life | 2 | small effect on subject's life |
| 2. | 2 | small effect on subject's life | 4 | small effect on subject's life |
| 3. | 13 | very large effect on subject's life | 5 | small effect on subject's life |
| 4. | 19 | very large effect on subject's life | 10 | moderate effect on subject's life |
| 5. | 1 | no effect at all on subject's life | 0 | no effect at all on subject's life |
| 6. | 6 | moderate effect on subject's life | 6 | moderate effect on subject's life |
| 7. | 6 | moderate effect on subject's life | 2 | small effect on subject's life |

TABLE 2-continued

| Subject's no. | DLQI scores (W 0) | Meaning of DLQI Scores | DLQI scores (W 16) | Meaning of DLQI Scores |
|---|---|---|---|---|
| 8. | 9 | moderate effect on subject's life | 2 | small effect on subject's life |
| 9. | 3 | small effect on subject's life | 3 | small effect on subject's life |
| 10. | 19 | very large effect on subject's life | 17 | very large effect on subject's life |
| 11. | 16 | very large effect on subject's life | 0 | no effect at all on subject's life |
| 12. | 12 | very large effect on subject's life | 8 | moderate effect on subject's life |
| 13. | 3 | small effect on subject's life | 7 | moderate effect on subject's life |
| 14. | 9 | moderate effect on subject's life | | Subject was included 4 weeks later |
| 15. | 1 | no effect at all on subject's life | | Subject was included 4 weeks later |
| 16. | 7 | moderate effect on subject's life | | Subject was included 8 weeks later |

TABLE 3

| Subject's no. | Before (W 0) | After 4 weeks (W 4) | Difference (W 4 − W 0) | Variation % |
|---|---|---|---|---|
| 1. | 4.81 | 3.80 | −1.01 | −21 |
| 2. | 1.00 | 0.61 | −0.39 | −39 |
| 3. | 2.00 | 2.00 | 0.00 | 0 |
| 4. | 3.41 | 1.80 | −1.61 | −47 |
| 5. | 1.80 | 1.61 | −0.19 | −11 |
| 6. | 1.80 | 0.61 | −1.19 | −66 |
| 7. | 3.41 | 3.80 | 0.39 | 11 |
| 8. | 4.81 | 1.40 | −3.41 | −71 |
| 9. | 1.80 | 1.00 | −0.80 | −44 |
| 10. | 1.80 | 1.71 | −0.09 | −5 |
| 11. | 1.21 | 0.81 | −0.40 | −33 |
| 12. | 4.50 | 3.41 | −1.09 | −24 |
| 13. | 2.21 | 2.21 | 0.00 | 0 |
| 14. | 0.31 | 0.31 | 0.00 | 0 |
| 15. | 0.21 | 0.21 | 0.00 | 0 |
| 16. | 3.00 | 1.80 | −1.20 | 40 |
| Mean | 2.38 | 1.69 | −0.69 | |
| Min | 0.21 | 0.21 | −3.41 | |
| Max | 4.81 | 3.80 | 0.39 | |
| SD | 1.47 | 1.16 | 0.93 | |
| Median | 1.90 | 1.66 | −.040 | |
| Δ % | | | −29% | |
| % subjects with positive effect | | | 69% | |

TABLE 4

| Subject's no. | Before (W 0) | After 8 weeks (W 8) | Difference (W 8 − W 0) | Variation % |
|---|---|---|---|---|
| 1. | 4.81* | no assessment | | |
| 2. | 1.00 | 0.61 | −0.39 | −39 |
| 3. | 2.00 | 1.61 | −0.39 | −20 |
| 4. | 3.41 | 1.21 | −2.20 | −65 |
| 5. | 1.80 | 1.80 | 0.00 | 0 |
| 6. | 1.80 | 2.00 | 0.20 | 11 |
| 7. | 3.41 | 3.21 | −0.20 | −6 |
| 8. | 4.81 | 1.40 | −3.41 | −71 |
| 9. | 1.80 | 1.00 | −0.80 | −44 |
| 10. | 1.80 | 2.80 | 1.00 | 56 |
| 11. | 1.21 | 0.81 | −0.40 | −33 |
| 12. | 4.50 | 2.21 | −2.29 | −51 |
| 13. | 2.21 | 1.40 | −0.81 | −37 |
| 14. | 0.31 | 0.11 | −0.20 | −65 |
| 15. | 0.21 | 0.11 | −0.10 | −48 |
| 16. | 3.00 | 1.80 | −1.20 | −40 |
| Mean | 2.22 | 1.47 | −0.75 | |
| Min | 0.21 | 0.11 | −3.41 | |
| Max | 4.81 | 3.21 | 1.00 | |
| SD | 1.37 | 0.89 | 1.12 | |
| Median | 1.80 | 1.40 | −0.39 | |
| Δ % | | | −34% | |
| % subjects with positive effect | | | 80% | |

TABLE 5

| Subject's no. | Before (W 0) | After 12 weeks (W 12) | Difference (W 12 − W 0) | Variation % |
|---|---|---|---|---|
| 1. | 4.81 | 7.20 | 2.39 | 50 |
| 2. | 1.00 | 0.61 | −0.39 | −39 |
| 3. | 2.00 | 1.21 | −0.79 | −40 |
| 4. | 3.41 | 2.21 | −1.20 | −35 |
| 5. | 1.80 | 0.61 | −1.19 | −65 |
| 6. | 1.80 | 0.31 | −1.49 | −83 |
| 7. | 3.41 | 3.60 | 0.19 | 6 |
| 8. | 4.81 | 1.80 | −3.01 | −63 |
| 9. | 1.80 | 1.21 | −0.59 | −33 |
| 10. | 1.80* | no assessment | | |
| 11. | 1.21 | 0.00 | −1.21 | −100 |
| 12. | 4.50 | 2.21 | −2.29 | −51 |
| 13. | 2.21 | 1.40 | −0.81 | −37 |
| 14. | 0.31 | 0.31 | 0.00 | 0 |
| 15. | 0.21 | 0.11 | −0.10 | −48 |
| 16. | | subject was included 8 weeks later | | |
| Mean | 2.38 | 1.63 | −0.75 | |
| Min | 0.21 | 0.00 | −3.01 | |
| Max | 4.81 | 7.20 | 2.39 | |
| SD | 1.57 | 1.89 | 1.26 | |
| Median | 1.90 | 1.21 | −0.80 | |
| Δ % | | | −32% | |
| % subjects with positive effect | | | 79% | |

TABLE 6

| Subject's no. | Before (W 0) | After 16 weeks (W 12) | Difference (W 16 − W 0) | Variation % |
|---|---|---|---|---|
| 1. | 4.81 | 6.00 | 1.19 | 25 |
| 2. | 1.00 | 0.61 | −0.39 | −39 |
| 3. | 2.00 | 1.21 | −0.79 | −40 |
| 4. | 3.41 | 1.80 | −1.61 | −47 |
| 5. | 1.80 | 0.61 | −1.19 | −66 |
| 6. | 1.80 | 0.31 | −1.49 | −83 |
| 7. | 3.41 | 3.60 | 0.19 | 6 |
| 8. | 4.81 | 1.80 | −3.01 | −63 |
| 9. | 1.80 | 0.31 | −1.49 | −83 |
| 10. | (1.80) | (9.50)* | (7.70)* | (428)* |
| 11. | 1.21 | 0.00 | −1.21 | −100 |
| 12. | 4.50 | 3.10 | −1.40 | −31 |
| 13. | 2.21 | 1.80 | −0.41 | −19 |
| 14. | | subject was included 4 weeks later | | |
| 15. | | subject was included 4 weeks later | | |
| 16. | | subject was included 8 weeks later | | |
| Mean | 2.73 | 1.76 | −0.97 | |
| Min | 1.00 | 0.00 | −3.01 | |
| Max | 4.81 | 6.00 | 1.19 | |
| SD | 1.40 | 1.74 | 1.05 | |
| Median | 2.11 | 1.51 | −1.20 | |
| Δ % | | | −35% | |
| % subjects with positive effect | | | 83% | |

TABLE 7

| Kinetics | PASI score (Mean ± SD) | p-value | Test type | Significance |
|---|---|---|---|---|
| Before (W 0) | 2.38 ± 1.47* | | | |
| 4th week (W 4) | 1.69 ± 1.16* | | | |
| 8th week (W 8) | 1.47 ± 0.89* | | | |
| 12th week (W 12) | 1.63 ± 1.89** | | | |
| 16th week (W 16) | 1.76 ± 1.74*** | | | |
| PASI score change (W 4 − W 0) | −0.29 ± 0.93* | 0.0047* | Wilcoxon | Yes |
| PASI score change (W 8 − W 0) | −0.75 ± 1.12* | 0.0222* | T-test | Yes |
| PASI score change (W 12 − W 0) | −0.75 ± 1.26** | 0.0439** | T-test | Yes |
| PASI score change (W 16 − W 0) | −0.97 ± 1.05*** | 0.0085*** | T-test | Yes |

Legend:
*the result was calculated for 16 subjects
**the result was calculated for 15 subjects
***the result was calculated for 13 subjects As seen in Tables 2, 3, 4 and 5 the test product significantly decreased the PASI score after 4, 8, 12 and 16 weeks, respectively, indicating an improvement in the skin condition. The results are further summarized in Table 6.

SUMMARY AND CONCLUSIONS

The test product was found to be well tolerated in the majority of subjects (13 out of 16). No indications of intolerance (such as irritation, burning sensation, redness or itching) were seen in these subjects, and the product did not cause skin dryness in the area of application. A significant improvement was seen with use of the test product, as determined by DLQI and PASI values.

The invention claimed is:

1. A galenic microbial composition comprising bacteria of the species *Propionibacterium freudenreichii*, or *Propionibacterium shermanii*, or the combination thereof, and a dermatologically compatible carrier that comprises an oily ingredient.

2. The galenic microbial composition according to claim 1, wherein said galenic microbial composition further comprises a dermatologically compatible antioxidant.

3. The galenic microbial composition according to claim 1, wherein said galenic microbial composition further comprises a carrier selected from the group consisting of water and aloe vera leaf juice or the combination thereof.

4. The galenic microbial composition according to claim 1, wherein said galenic microbial composition further comprises at least one excipient selected from the group consisting of a thickener, a preservative, a neutralizer, a humectant, an emulsifier, an occlusive, a coemulsifier, an antioxidant, a fragrance and any combination thereof.

* * * * *